US011346836B2

(12) United States Patent
Foster et al.

(10) Patent No.: US 11,346,836 B2
(45) Date of Patent: May 31, 2022

(54) SMALL APERTURE LARGE ELECTRODE CELL

(71) Applicant: Roche Sequencing Solutions, Inc., Pleasanton, CA (US)

(72) Inventors: John Foster, Mountain View, CA (US); Morgan Mager, Sunnyvale, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 0 days.

(21) Appl. No.: 16/948,401

(22) Filed: Sep. 16, 2020

(65) Prior Publication Data
US 2021/0072221 A1 Mar. 11, 2021

Related U.S. Application Data

(62) Division of application No. 14/841,127, filed on Aug. 31, 2015, now Pat. No. 10,809,243.

(51) Int. Cl.
H01L 29/40 (2006.01)
G01N 27/447 (2006.01)
G01N 33/487 (2006.01)

(52) U.S. Cl.
CPC . *G01N 33/48721* (2013.01); *G01N 27/44791* (2013.01); *H01L 29/401* (2013.01)

(58) Field of Classification Search
CPC .......... G01N 33/004; G01N 33/48721; G01N 29/401; G01N 27/3272; G01N 27/3278; G01N 27/4146; G01N 27/44791
See application file for complete search history.

(56) References Cited

U.S. PATENT DOCUMENTS 7,217,520 B2  5/2007  Tsinberg et al.
7,833,396 B2  11/2010 Fukushima
(Continued)

FOREIGN PATENT DOCUMENTS

EP     1712891 A2  10/2006
WO  2013063126 A2   5/2013
(Continued)

OTHER PUBLICATIONS

Crescentini, et al_a distributed amplifier system for bilayer lipid membrane (BLM? Arrays with noise and Individual Offset Cancellation_ IEEE Transactions on Biomedical Circuits and Systems, vol. 9 No. 3, Jun. 2015.
(Continued)

*Primary Examiner* — Mayla Gonzalez Ramos
(74) *Attorney, Agent, or Firm* — Winston Chu

(57) ABSTRACT

A nanopore cell includes a conductive layer and a working electrode disposed above the conductive layer and at the bottom of a well into which an electrolyte may be contained, such that at least a portion of a top base surface area of the working electrode is exposed to the electrolyte. The nanopore cell further includes a first insulating wall disposed above the working electrode and surrounding a lower section of a well, and a second insulating wall disposed above the first insulating wall and surrounding an upper section of the well, forming an overhang above the lower section of the well. The upper section of the well includes an opening that a membrane may span across, and wherein a base surface area of the opening is smaller than the at least a portion of the top base surface area of the working electrode that is exposed to the electrolyte.

8 Claims, 20 Drawing Sheets

(56) References Cited

U.S. PATENT DOCUMENTS

| | | |
|---|---|---|
| 2004/0022677 A1 | 2/2004 | Wohlstadter et al. |
| 2005/0079598 A1 | 4/2005 | Davis |
| 2006/0231419 A1* | 10/2006 | Barth .................. C12Q 1/6825 205/775 |
| 2007/0105089 A1 | 5/2007 | Deutsch |
| 2008/0237674 A1 | 10/2008 | Ueda |
| 2009/0140799 A1 | 6/2009 | Kasperkovitz |
| 2009/0199960 A1 | 8/2009 | Nuzzo et al. |
| 2010/0331194 A1 | 12/2010 | Turner et al. |
| 2013/0087467 A1 | 4/2013 | Yang |
| 2013/0115137 A1 | 5/2013 | Tao et al. |
| 2013/0325096 A1 | 12/2013 | Dupelle et al. |
| 2013/0325380 A1 | 12/2013 | Dehnke, II et al. |
| 2014/0034497 A1* | 2/2014 | Davis ............... G01N 27/44791 204/451 |
| 2014/0183667 A1 | 7/2014 | Chang et al. |

FOREIGN PATENT DOCUMENTS

| | | |
|---|---|---|
| WO | 2013123450 A1 | 8/2013 |
| WO | 2013191793 A1 | 12/2013 |
| WO | 2015/057324 A2 | 4/2015 |
| WO | 2015061510 A1 | 4/2015 |
| WO | 2016/122797 A1 | 8/2016 |

OTHER PUBLICATIONS

Ogier et al_Suspended Planar Phospholipid Bilayers on Micromachined Supports_Langmuir 2000 16, 5696-5701.

Saha Shimul Chandra et al, Scalable Micro-Cavity bilayer lipid membrane arrays for parallel ion channel recording_Sensors and Actuators_col. 199 pp. 76-82_2014.

* cited by examiner

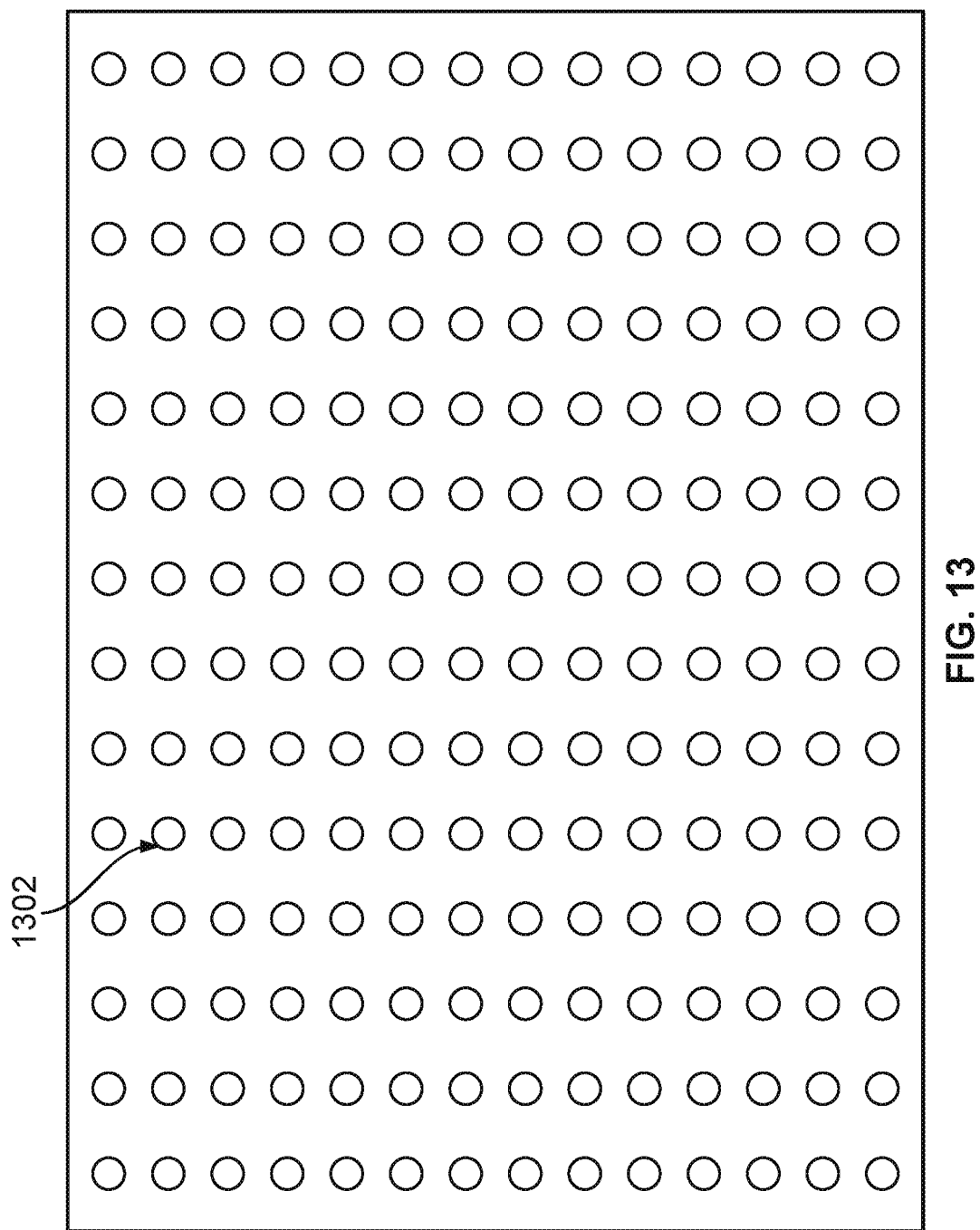

US 11,346,836 B2

SMALL APERTURE LARGE ELECTRODE CELL

CROSS REFERENCE TO RELATED APPLICATIONS

This application is a divisional application of U.S. patent application Ser. No. 14/841,127, filed Aug. 31, 2015 and titled "SMALL APERTURE LARGE ELECTRODE CELL," which is herein incorporated by reference in its entirety for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

FIG. 13 illustrates an embodiment of a process for constructing a non-faradaic electrochemical cell of a nanopore based sequencing chip that includes a TiN working electrode with increased electrochemical capacitance.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
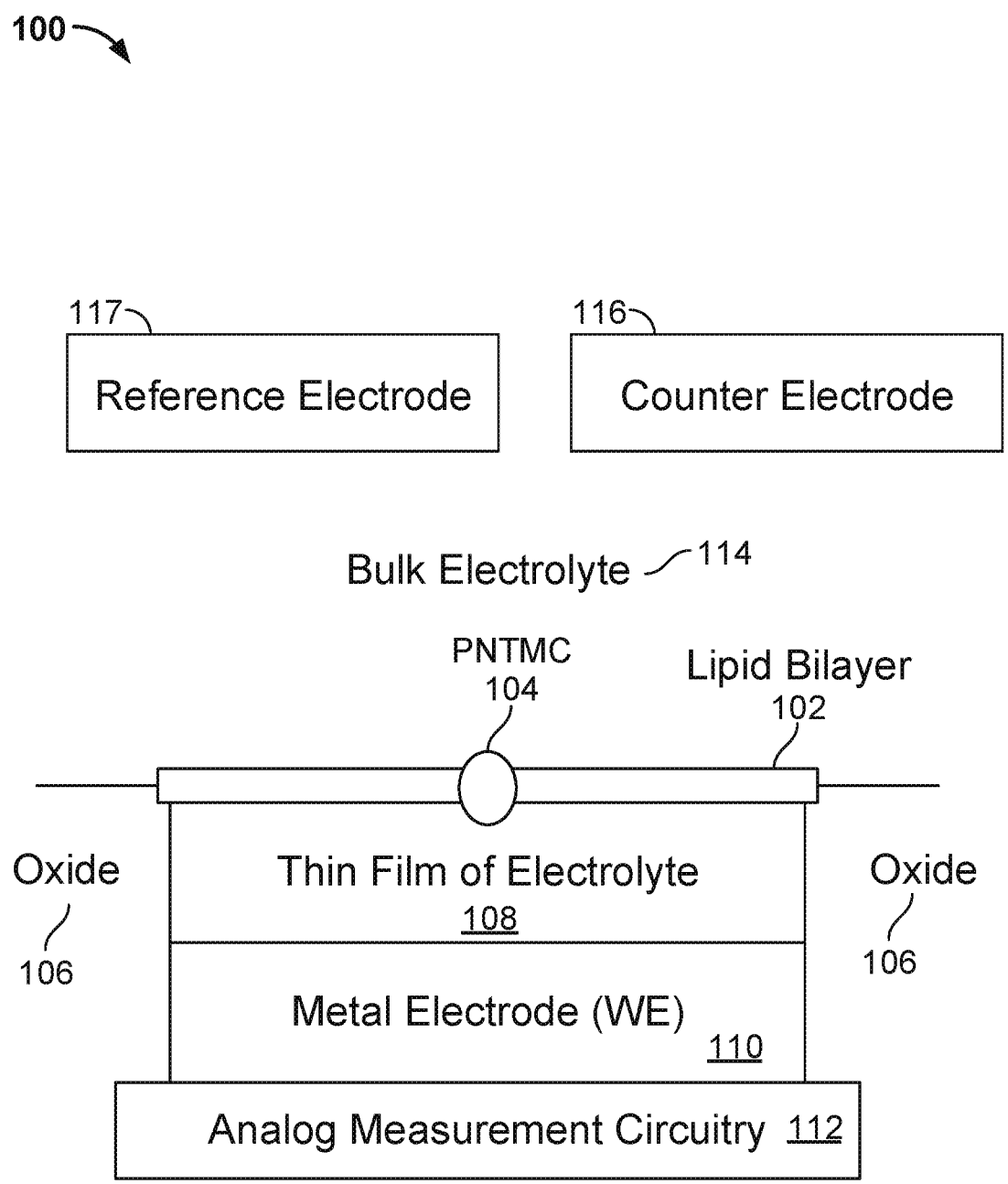
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to an electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116. The cell also includes a reference electrode 117, which acts as an electrochemical potential sensor.

Figure 2:
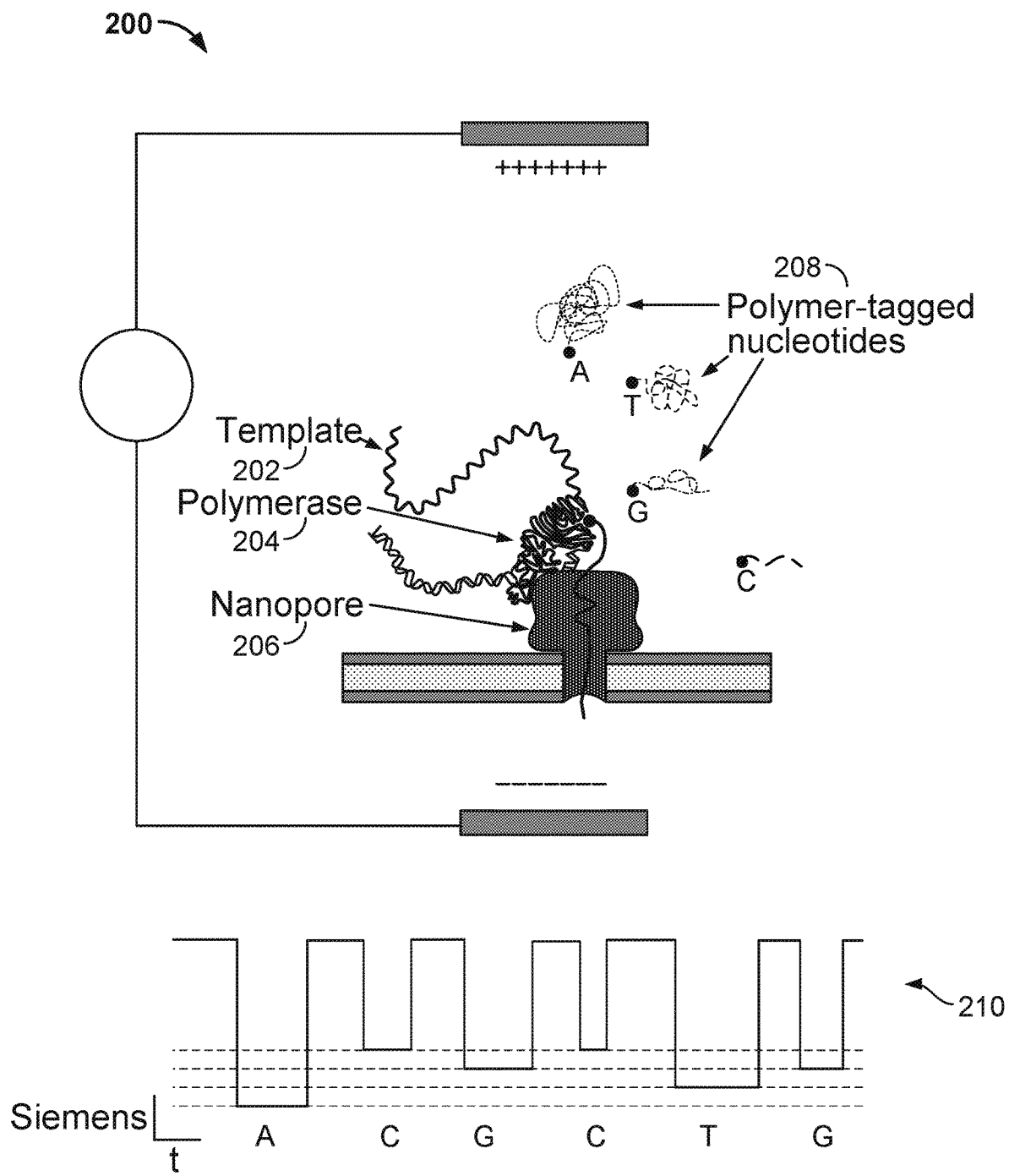
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
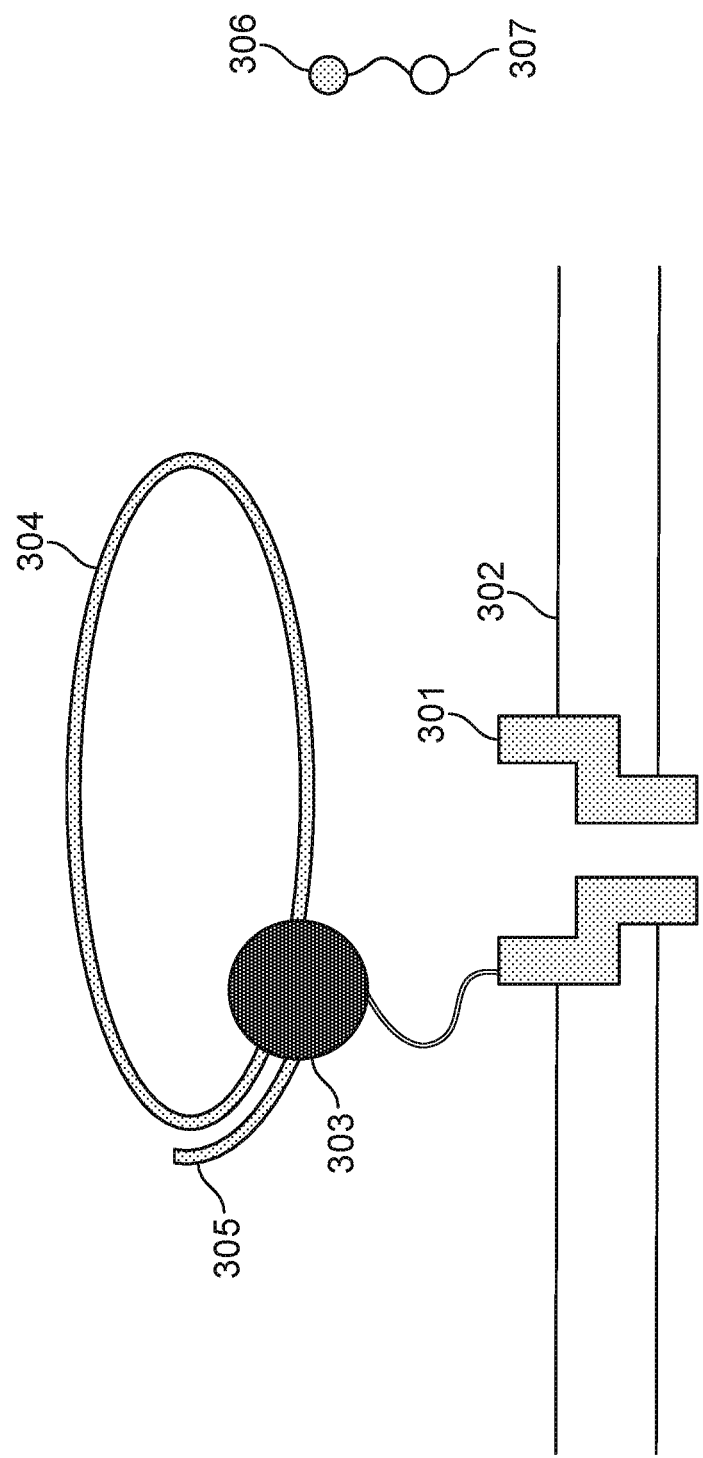
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
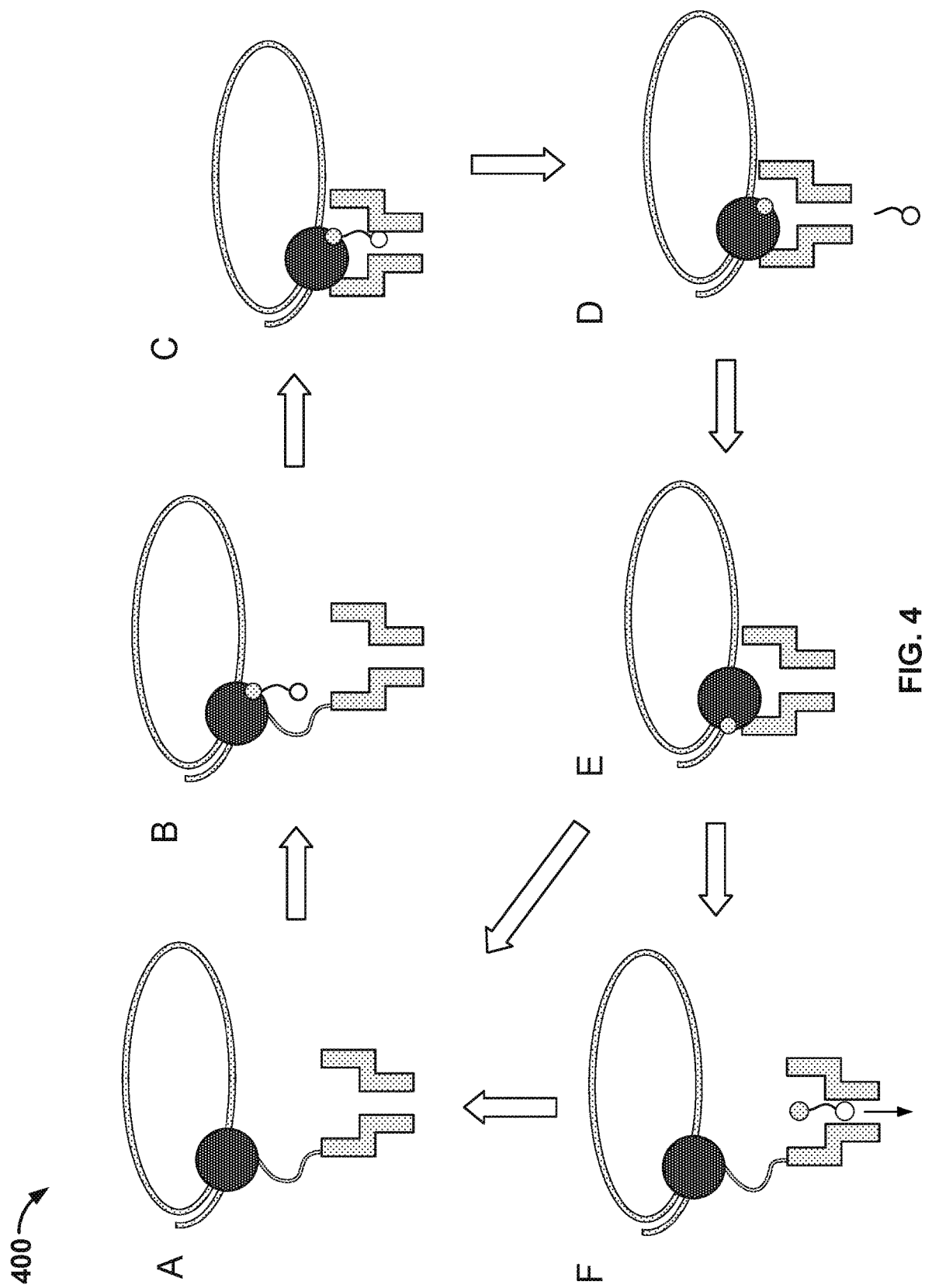
FIG. 4 illustrates an embodiment of a process 400 for nucleic acid sequencing with pre-loaded tags.

FIG. 4 illustrates an embodiment of a process 400 for nucleic acid sequencing with pre-loaded tags. At stage A, a tagged nucleotide (one of four different types: A, T, G, or C) is not associated with the polymerase. At stage B, a tagged nucleotide is associated with the polymerase. At stage C, the polymerase is in close proximity to the nanopore. The tag is pulled into the nanopore by an electrical field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage B.

Before the polymerase is docked to the nanopore, the conductance of the nanopore is ~300 pico Siemens (300 pS). At stage C, the conductance of the nanopore is about 60 pS, 80 pS, 100 pS, or 120 pS corresponding to one of the four types of tagged nucleotides. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
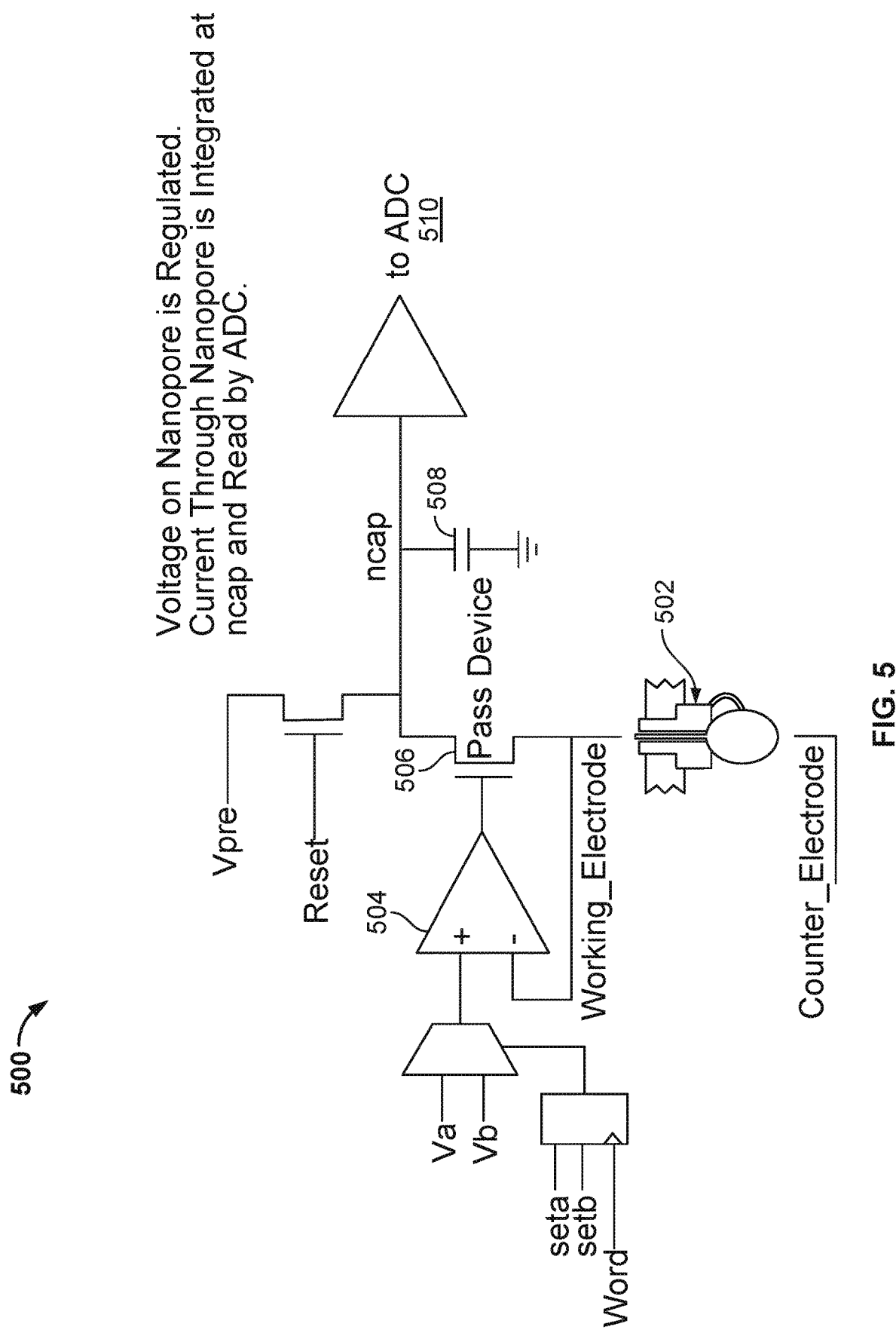
FIG. 5 illustrates an embodiment of a circuitry 500 in a cell of a nanopore based sequencing chip.

FIG. 5 illustrates an embodiment of a circuitry 500 in a cell of a nanopore based sequencing chip. As mentioned above, when the tag is held in nanopore 502, a unique conductance signal (e.g., see signal 210 in FIG. 2) is generated due to the tag's distinct chemical structures, thereby identifying the added base electronically. The circuitry in FIG. 5 maintains a constant voltage across nanopore 502 when the current flow is measured. In particular, the circuitry includes an operational amplifier 504 and a pass device 506 that maintain a constant voltage equal to $V_a$ or $V_b$ across nanopore 502. The current flowing through nanopore 502 is integrated at a capacitor $n_{cap}$ 508 and measured by an Analog-to-Digital (ADC) converter 510.

However, circuitry 500 has a number of drawbacks. One of the drawbacks is that circuitry 500 only measures unidirectional current flow. Another drawback is that operational amplifier 504 in circuitry 500 may introduce a number of performance issues. For example, the offset voltage and the temperature drift of operational amplifier 504 may cause the actual voltage applied across nanopore 502 to vary across different cells. The actual voltage applied across nanopore 502 may drift by tens of millivolts above or below the desired value, thereby causing significant measurement inaccuracies. In addition, the operational amplifier noise may cause additional detection errors. Another drawback is that the portions of the circuitry for maintaining a constant voltage across the nanopore while current flow measurements are made are area-intensive. For example, operational amplifier 504 occupies significantly more space in a cell than other components. As the nanopore based sequencing chip is scaled to include more and more cells, the area occupied by the operational amplifiers may increase to an unattainable size. Unfortunately, shrinking the operational amplifier's size in a nanopore based sequencing chip with a large-sized array may raise other performance issues. For example, it may exacerbate the offset and noise problems in the cells even further.

Figure 6:
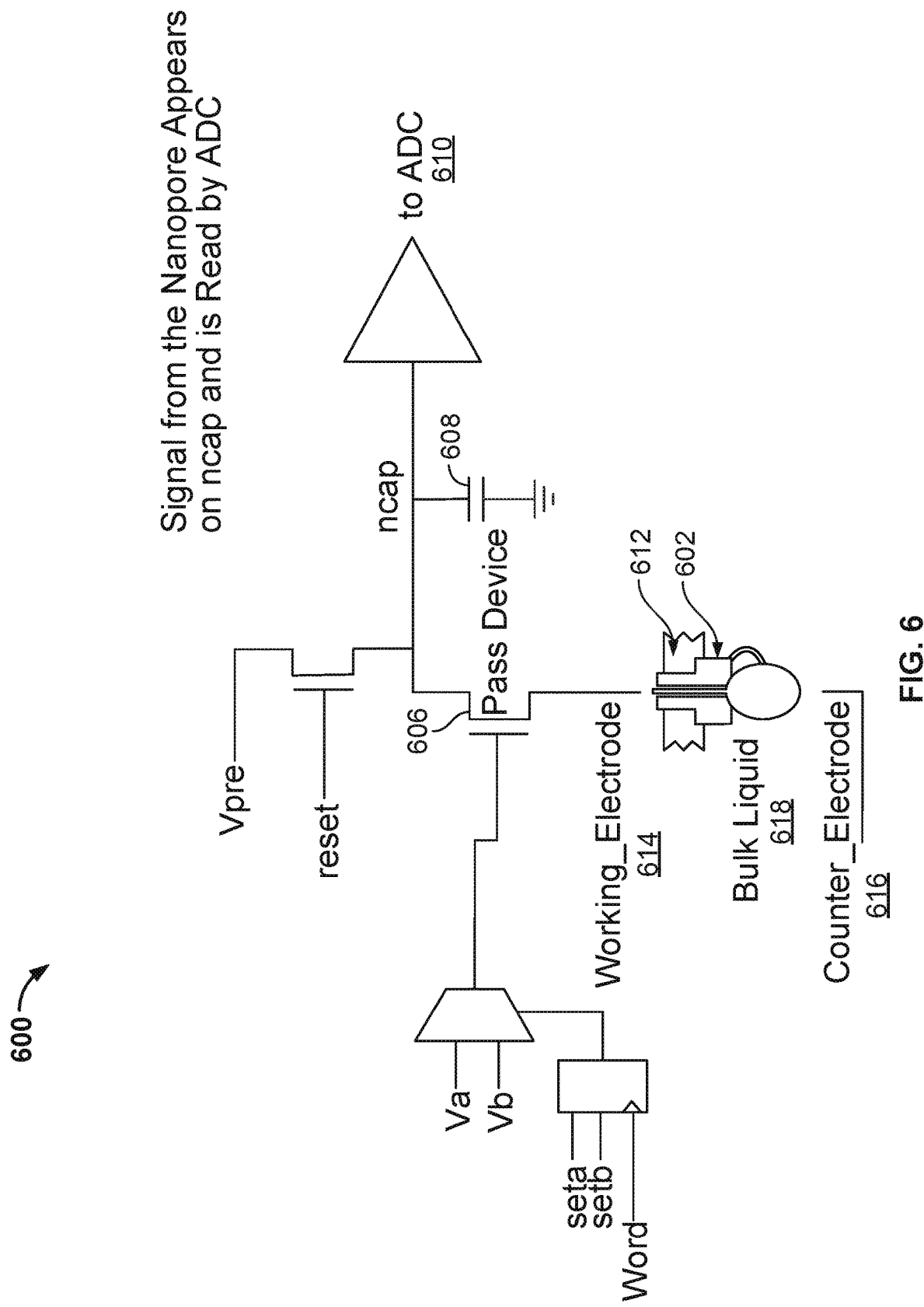
FIG. 6 illustrates an embodiment of a circuitry 600 in a cell of a nanopore based sequencing chip, wherein the voltage applied across the nanopore can be configured to vary over a time period during which the nanopore is in a particular detectable state.
Figure 7A:
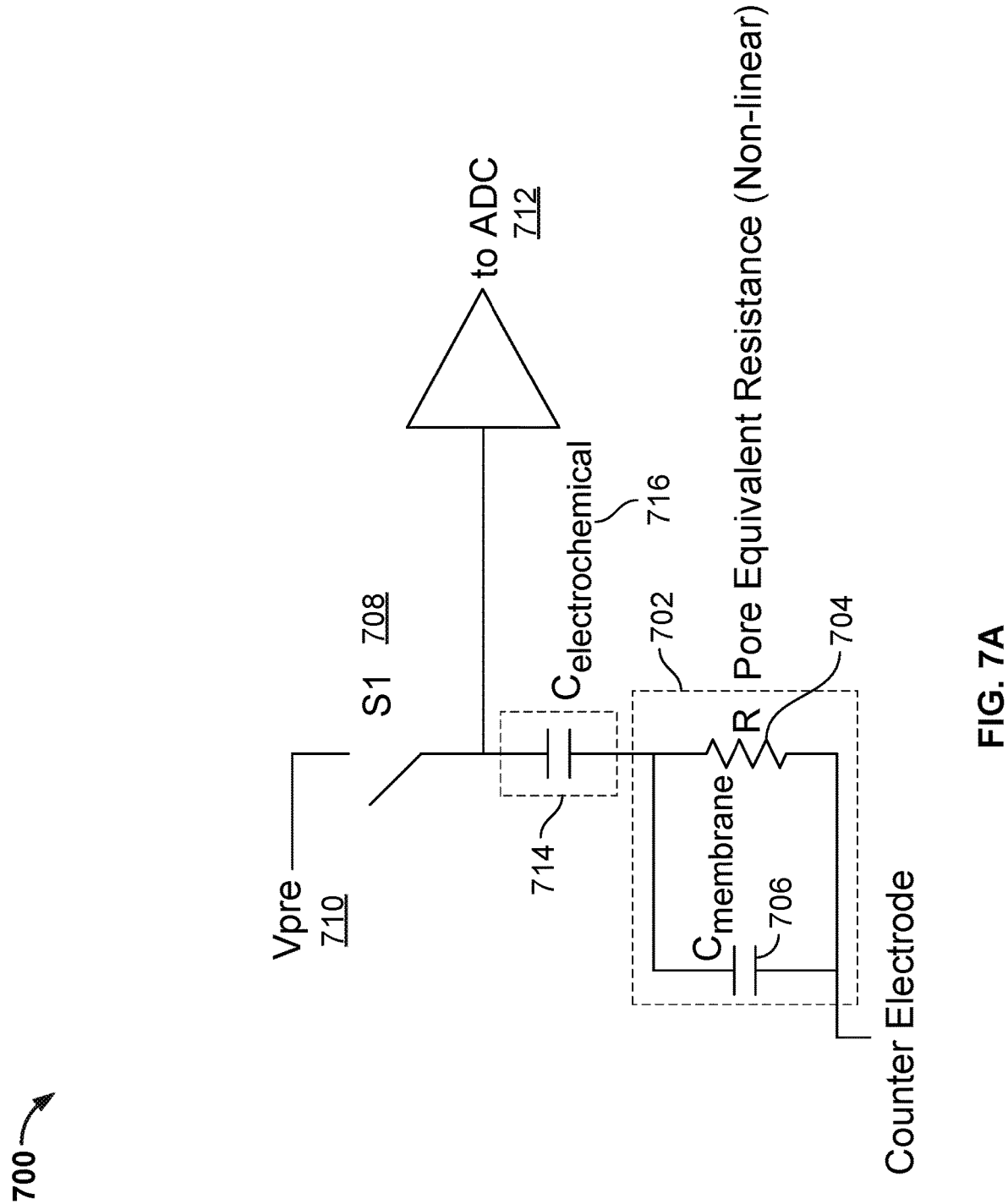
FIG. 7A illustrates an additional embodiment of a circuitry 700 in a cell of a nanopore based sequencing chip, wherein the voltage applied across the nanopore can be configured to vary over a time period during which the nanopore is in a particular detectable state.
Figure 7B:
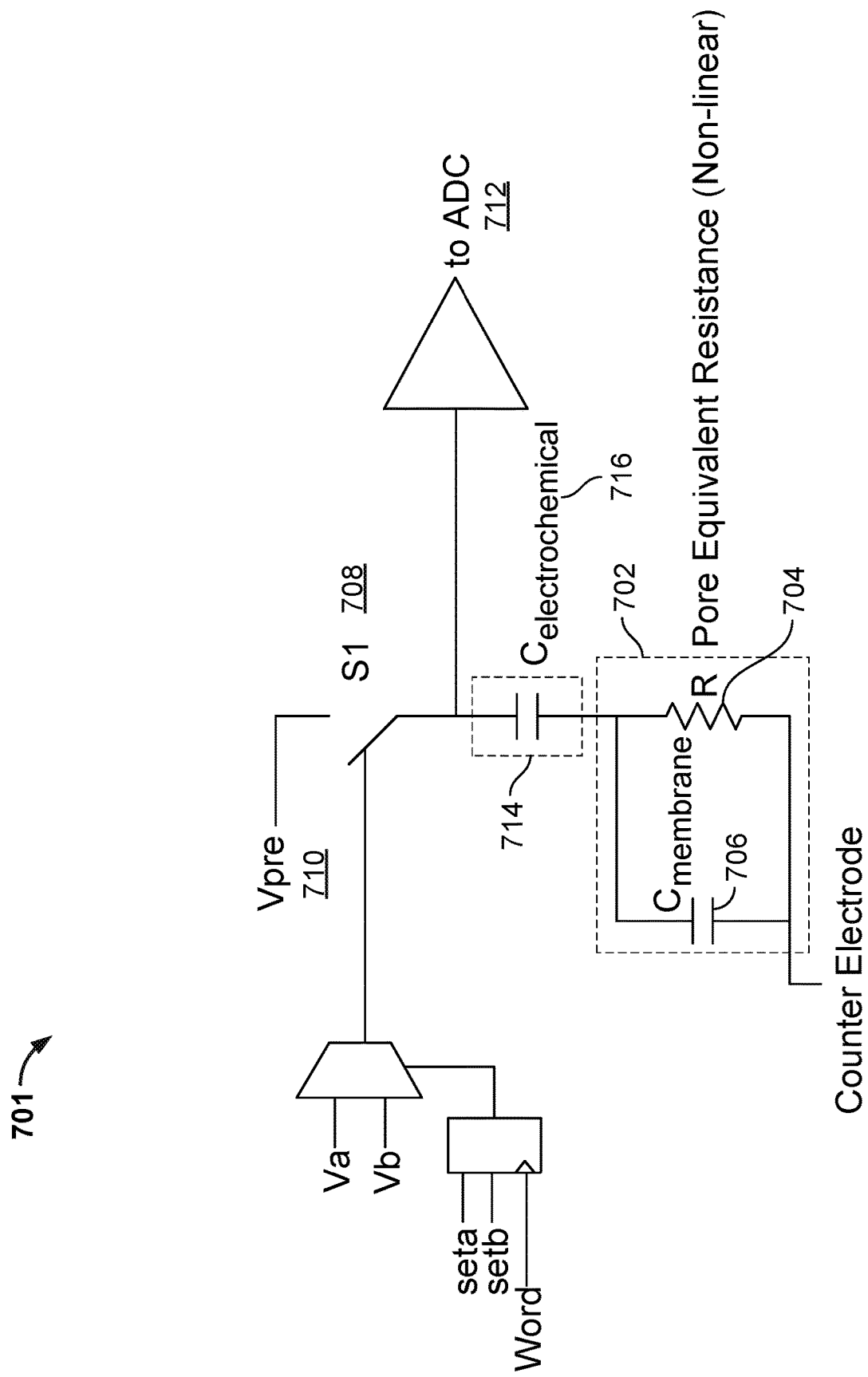
FIG. 7B illustrates an additional embodiment of a circuitry 701 in a cell of a nanopore based sequencing chip, wherein the voltage applied across the nanopore can be configured to vary over a time period during which the nanopore is in a particular detectable state.

FIG. 6 illustrates an embodiment of a circuitry 600 in a cell of a nanopore based sequencing chip, wherein the voltage applied across the nanopore can be configured to vary over a time period during which the nanopore is in a particular detectable state. One of the possible states of the nanopore is an open-channel state when a tag-attached polyphosphate is absent from the barrel of the nanopore. Another four possible states of the nanopore correspond to the states when the four different types of tag-attached polyphosphate (A, T, G, or C) are held in the barrel of the nanopore. Yet another possible state of the nanopore is when the membrane is ruptured. FIGS. 7A and 7B illustrate additional embodiments of a circuitry (700 and 701) in a cell of a nanopore based sequencing chip, wherein the voltage applied across the nanopore can be configured to vary over a time period during which the nanopore is in a particular detectable state. In the above circuits, the operational amplifier is no longer required.

FIG. 6 shows a nanopore 602 that is inserted into a membrane 612, and nanopore 602 and membrane 612 are situated between a cell working electrode 614 and a counter electrode 616, such that a voltage is applied across nanopore 602. Nanopore 602 is also in contact with a bulk liquid/electrolyte 618. Note that nanopore 602 and membrane 612 are drawn upside down as compared to the nanopore and membrane in FIG. 1. Hereinafter, a cell is meant to include at least a membrane, a nanopore, a working cell electrode, and the associated circuitry. In some embodiments, the counter electrode is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells. There is a working cell electrode within each measurement cell; in contrast to the common electrode, working cell electrode 614 is configurable to apply a distinct potential that is independent from the working cell electrodes in other measurement cells.

In FIGS. 7A and 7B, instead of showing a nanopore inserted in a membrane and the liquid surrounding the nanopore, an electrical model 702 representing the electrical properties of the nanopore and the membrane and an electrical model 714 representing the electrical properties of the working electrode are shown. Note in FIGS. 7A and 7B that the respective circuitry does not require an extra capacitor (e.g., $n_{cap}$ 508 in FIG. 5) to be fabricated on-chip, thereby facilitating the reduction in size of the nanopore based sequencing chip.

Electrical model 702 includes a capacitor 706 that models a capacitance associated with the membrane ($C_{membrane}$) and a resistor 704 that models a resistance associated with the nanopore in different states (e.g., the open-channel state or the states corresponding to having different types of tags or molecules inside the nanopore). Electrical model 714 includes a capacitor 716 that models a capacitance associated with the working electrode. The capacitance associated with the working electrode is also referred to as an electrochemical capacitance ($C_{electrochemical}$). The electrochemical capacitance $C_{electrochemical}$ associated with the working electrode includes a double-layer capacitance and may further include a pseudocapacitance.

Figure 7C:
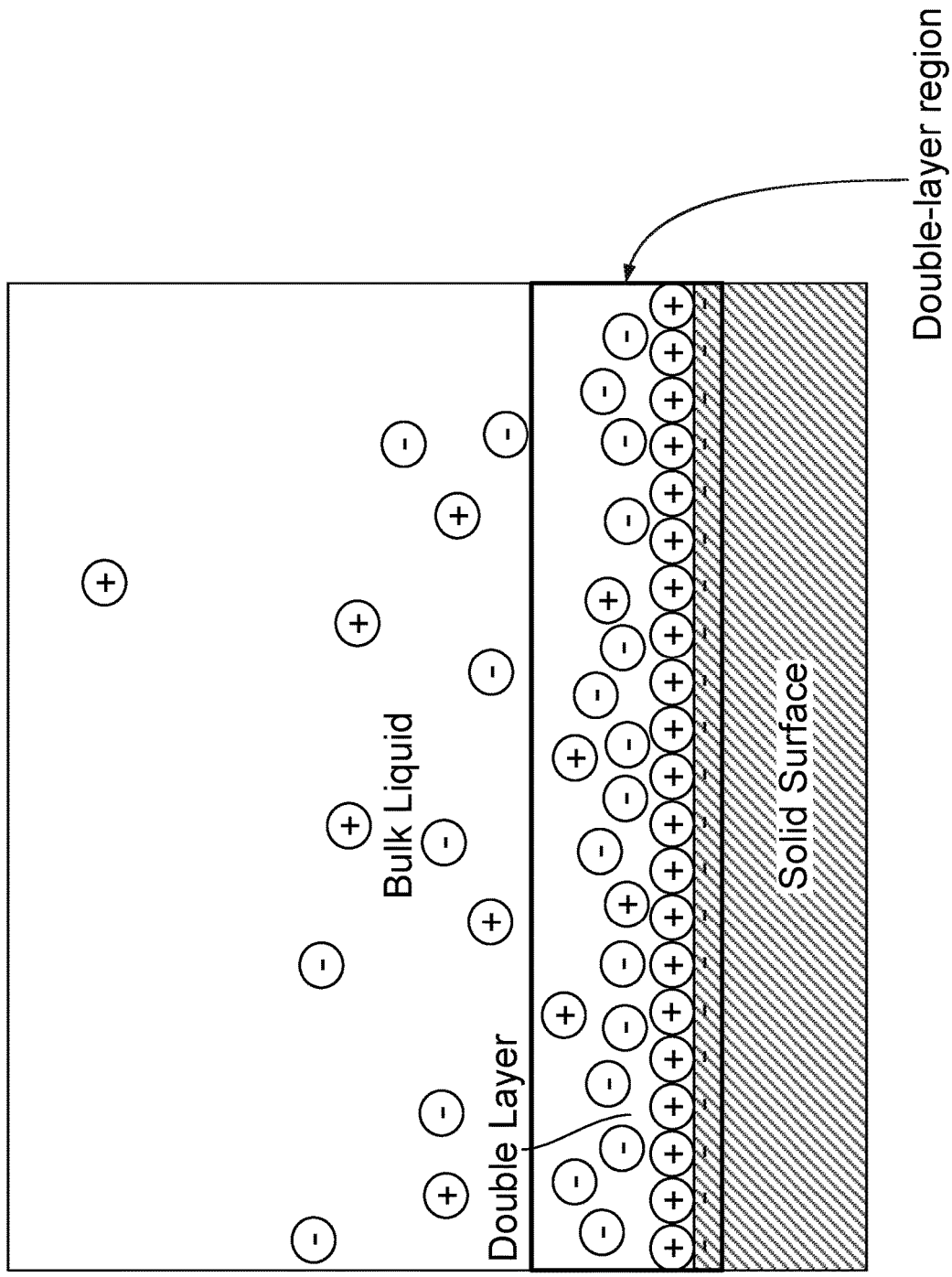
FIG. 7C illustrates a double layer that is formed at any interface between a conductive electrode and an adjacent liquid electrolyte. In the example shown, the electrode surface is negatively charged, resulting in the accumulation of positively charged species in the electrolyte. In another example, the polarity of all charges shown may be opposite to the example shown.
Figure 7D:
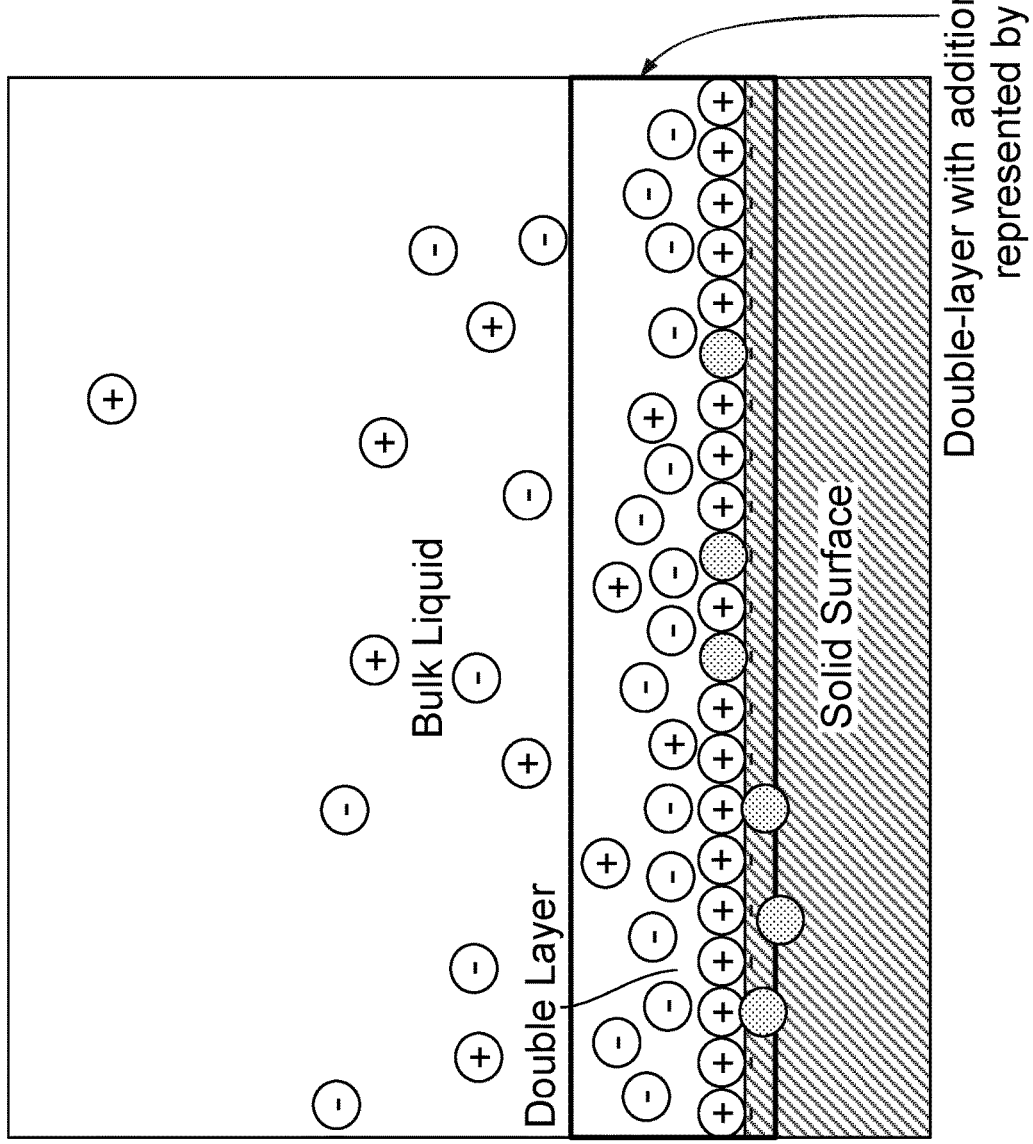
FIG. 7D illustrates a pseudocapacitance effect that can be formed, simultaneously with the formation of a double-layer as in FIG. 7C, at an interface between a conductive electrode and an adjacent liquid electrolyte.

FIG. 7C illustrates a double layer that is formed at any interface between a conductive electrode and an adjacent liquid electrolyte. If a voltage is applied, electronic charges (positive or negative) accumulate in the electrode at the interface between the conductive electrode and adjacent liquid electrolyte. The charge in the electrode is balanced by reorientation of dipoles and accumulation of ions of opposite charge in the electrolyte near the interface. The accumulation of charges on either side of the interface between electrode and electrolyte, separated by a small distance due to the finite size of charged species and solvent molecules in the electrolyte, acts like a dielectric in a conventional capacitor. The term "double layer" refers to the ensemble of electronic and ionic charge distribution in the vicinity of the interface between the electrode and electrolyte. FIG. 7D illustrates a pseudocapacitance effect that can be formed, simultaneously with the formation of a double-layer as in FIG. 7C, at an interface between a conductive electrode and an adjacent liquid electrolyte. A pseudocapacitor stores electrical energy faradaically by electron charge transfer between the electrode and the electrolyte. This is accomplished through electrosorption, reduction-oxidation reactions, or intercalation processes.

Figure 8:
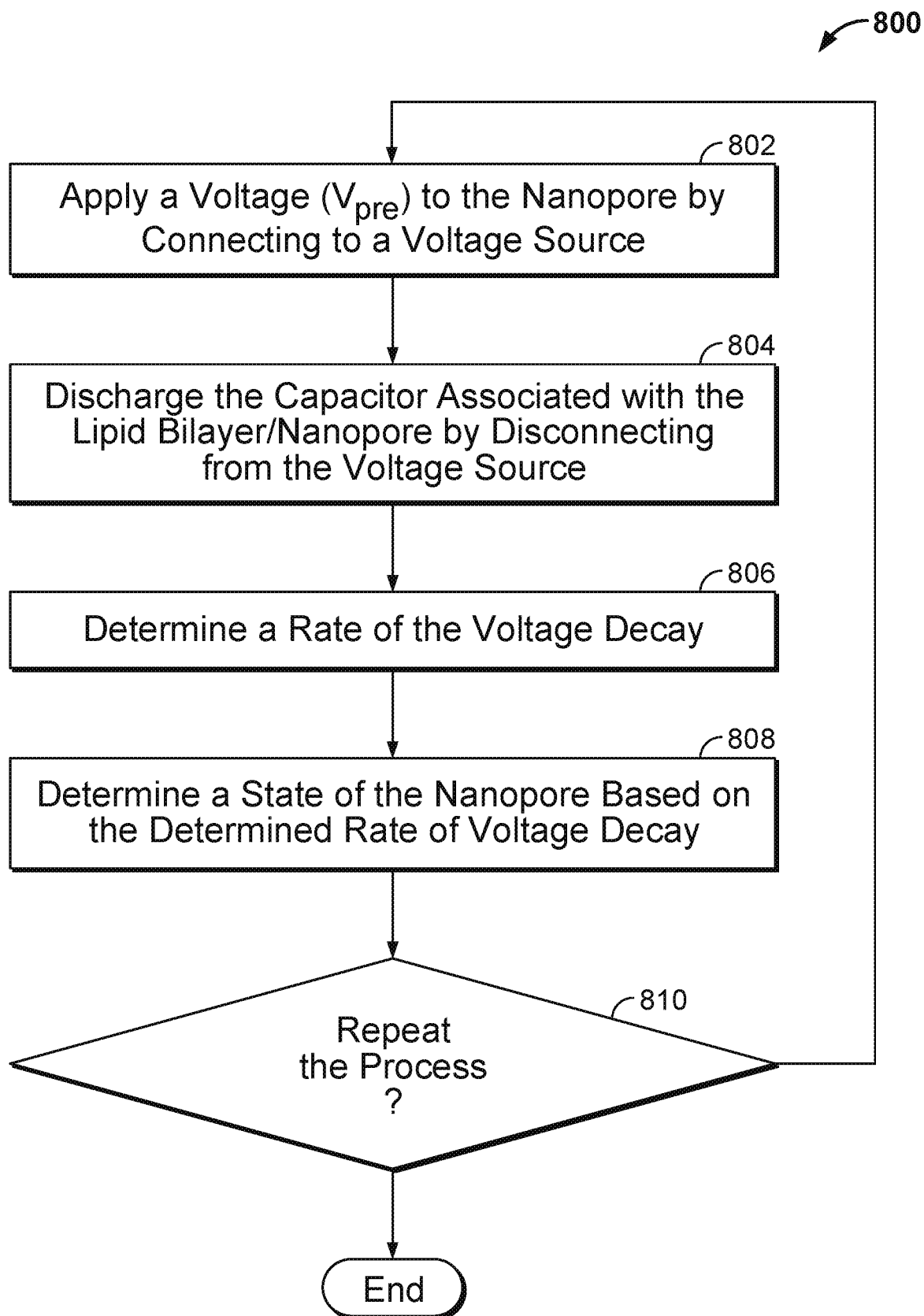
FIG. 8 illustrates an embodiment of a process 800 for analyzing a molecule inside a nanopore, wherein the nanopore is inserted in a membrane.
Figure 9:
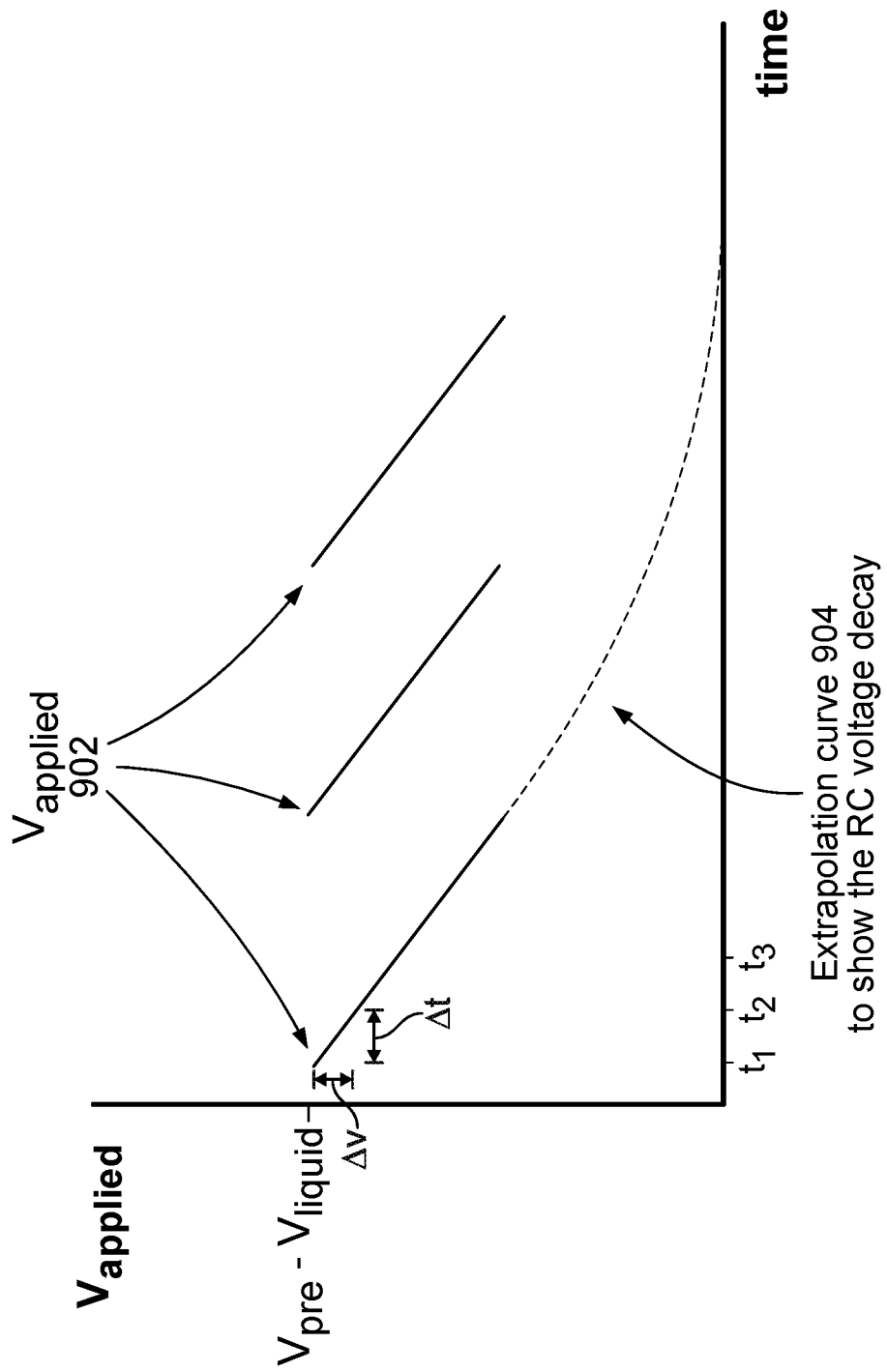
FIG. 9 illustrates an embodiment of a plot of the voltage applied across the nanopore versus time when process 800 is performed and repeated three times.

FIG. 8 illustrates an embodiment of a process 800 for analyzing a molecule inside a nanopore, wherein the nanopore is inserted in a membrane. Process 800 may be performed using the circuitries shown in FIG. 6, 7A, or 7B. FIG. 9 illustrates an embodiment of a plot of the voltage applied across the nanopore versus time when process 800 is performed and repeated three times. The voltage across the nanopore changes over time. The rate of the voltage decay (i.e., the steepness of the slope of the voltage across the nanopore versus time plot) depends on the cell resistance (e.g., the resistance of resistor 704 in FIG. 7A). More particularly, as the resistances associated with the nanopore in different states (e.g., the states corresponding to having different types of molecules inside the nanopore) are different due to the molecules' distinct chemical structure, different corresponding rates of voltage decay may be observed and thus may be used to identify the molecule in the nanopore.

Figure 10:
FIG. 10 illustrates an embodiment of the plots of the voltage applied across the nanopore versus time when the nanopore is in different states.

FIG. 10 illustrates the plots of the voltage applied across the nanopore versus time when the nanopore is in different states. Curve 1002 shows the rate of voltage decay during an open-channel state. In some embodiments, the resistance associated with the nanopore in an open-channel state is in the range of 100 Mohm to 20 Gohm. Curves 1004, 1006, 1008, and 1010 show the different rates of voltage decay corresponding to the four capture states when the four different types of tag-attached polyphosphate (A, T, G, or C) are held in the barrel of the nanopore. In some embodiments, the resistance associated with the nanopore in a capture state is within the range of 200 Mohm to 40 Gohm. Note that the slope of each of the plots is distinguishable from each other.

Allowing the voltage applied across the nanopore to decay over a time period during which the nanopore is in a particular detectable state has many advantages. One of the advantages is that the elimination of the operational amplifier, the pass device, and the capacitor (e.g., $n_{cap}$ 508 in FIG. 5) that are otherwise fabricated on-chip in the cell circuitry significantly reduces the footprint of a single cell in the nanopore based sequencing chip, thereby facilitating the scaling of the nanopore based sequencing chip to include more and more cells (e.g., incorporating millions of cells in a nanopore based sequencing chip). The capacitance in parallel with the nanopore includes two portions: the capacitance associated with the membrane and the capacitance associated with the integrated chip (IC). Due to the thin nature of the membrane, the capacitance associated with the membrane alone can suffice to achieve the required RC time constant without the need for additional on-chip capacitance, thereby allowing significant reduction in cell size and chip size.

Another advantage is that the circuitry of a cell does not suffer from offset inaccuracies because $V_{pre}$ is applied directly to the working electrode without any intervening circuitry. Another advantage is that since no switches are being opened or closed during the measurement intervals, the amount of charge injection is minimized.

Furthermore, the technique described above operates equally well using positive voltages or negative voltages. Bidirectional measurements have been shown to be helpful in characterizing a molecular complex. For example, they can be used to correct for baseline drift arising from AC-non-faradaic operation.

The ratio of the capacitance associated with the membrane (see $C_{membrane}$ 706 of FIGS. 7A and 7B) and the capacitance associated with the working electrode (see C electrochemical 716 of FIGS. 7A and 7B) may be adjusted to achieve optimal overall system performance. Increased system performance may be achieved by reducing $C_{membrane}$ while maximizing $C_{electrochemical}$. For example, $C_{membrane}$ is adjusted to achieve the required RC time constant without the need for additional on-chip capacitance, thereby allowing a significant reduction in cell size and chip size. C electrochemical is maximized such that the impedance associated with $C_{electrochemical}$ is close to an AC (alternating current) short circuit compared with the impedance associated with $C_{membrane}$. $C_{electrochemical}$ is also maximized such that the information signal measured by the circuitries shown in FIG. 6, 7A, or 7B becomes more stable and that the spurious signal convoluted on top of the information signal is minimized.

Figure 11:
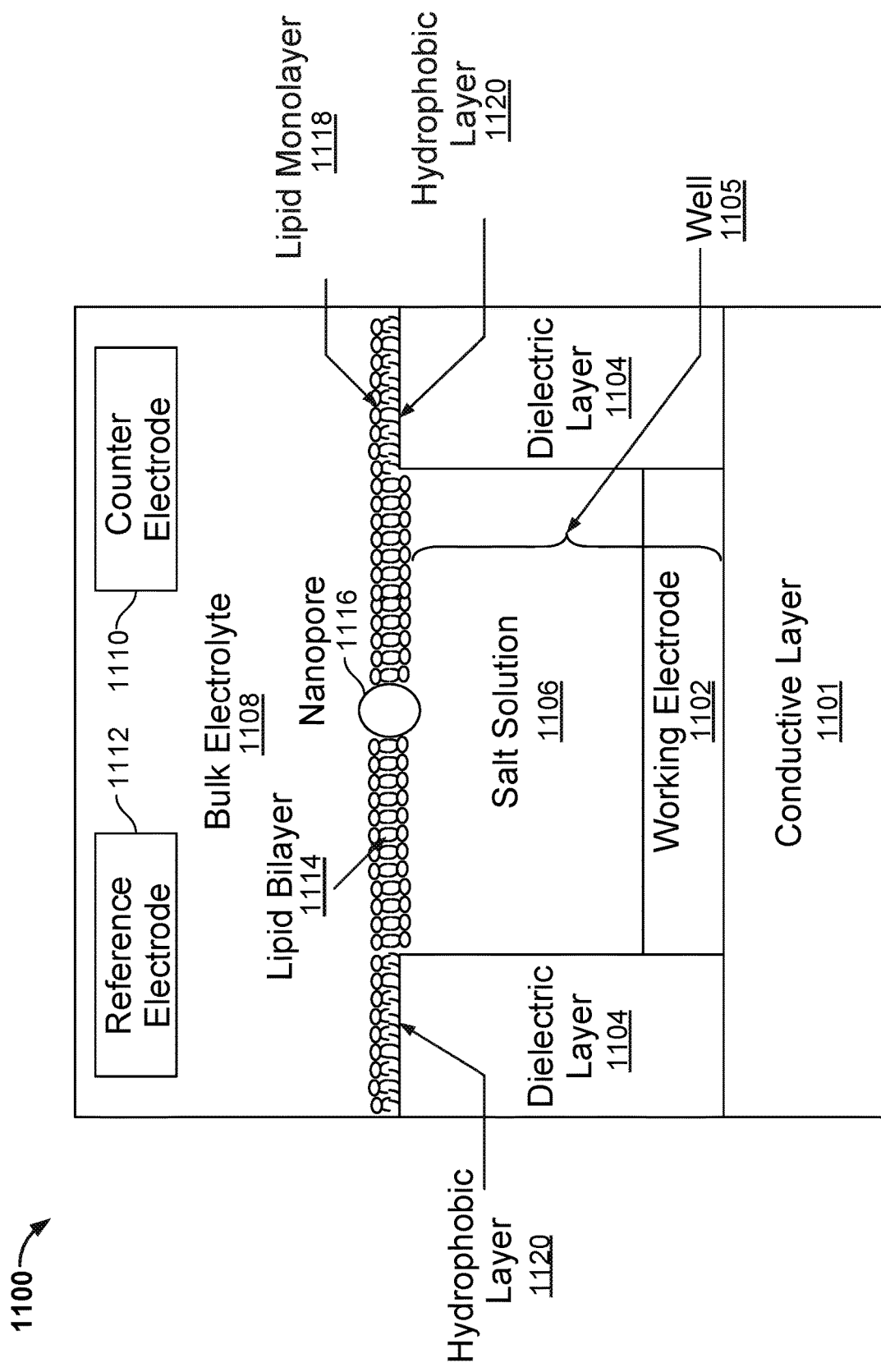
FIG. 11 illustrates an embodiment of a non-faradaic electrochemical cell 1100 of a nanopore based sequencing chip that includes a TiN working electrode with increased electrochemical capacitance.

FIG. 11 illustrates an embodiment of a cell 1100 in a nanopore based sequencing chip. In this embodiment, the ratio of the $C_{membrane}$ and $C_{electrochemical}$ may be adjusted by increasing $C_{electrochemical}$, as will be described in greater detail below.

Cell 1100 includes a conductive or metal layer 1101. Metal layer 1101 connects cell 1100 to the remaining portions of the nanopore based sequencing chip. In some embodiments, metal layer 1101 is the metal 6 layer (M6). Cell 1100 further includes a dielectric layer 1104 above conductive layer 1101. Dielectric layer 1104 forms the walls surrounding a well 1105 in which a working electrode 1102 is located at the bottom. In some embodiments, working electrode 1102 is made of materials that are resistant to corrosion and oxidation for non-faradaic conduction. The top surface of dielectric layer 1104 may be silanized. Silanization forms a hydrophobic layer 1120 above the top surface of dielectric layer 1104. Well 1105 formed by the dielectric layer walls 1104 further includes a film of salt solution 1106 above working electrode 1102.

As shown in FIG. 11, a membrane is formed on top of dielectric layer 1104 and spans across well 1105. For example, the membrane includes a lipid monolayer 1118 formed on top of hydrophobic layer 1120. As the membrane reaches the opening of well 1105, the lipid monolayer transitions to a lipid bilayer 1114 that spans across the opening of the well. A bulk electrolyte 1108 containing protein nanopore transmembrane molecular complexes (PNTMC) and the analyte of interest is placed directly above the well. A single PNTMC/nanopore 1116 is inserted into lipid bilayer 1114 by electroporation. Nanopore 1116 crosses lipid bilayer 1114 and provides the only path for ionic flow from bulk electrolyte 1108 to working electrode 1102.

Cell 1100 includes a counter electrode (CE) 1110. Cell 1100 also includes a reference electrode 1112, which acts as an electrochemical potential sensor. In some embodiments, counter electrode 1110 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

As discussed above, the ratio of $C_{membrane}$ and $C_{electrochemical}$ in cell 1100 may be adjusted by increasing $C_{electrochemical}$. The electrochemical capacitance ($C_{electrochemical}$) associated with working electrode 1102 may be increased by increasing the thickness of working electrode 1102. In some embodiments, the thickness of working electrode 1102 ranges from 10 nanometers to 1 micron.

$C_{electrochemical}$ may also be increased by maximizing the specific surface area of the electrode. The specific surface area of working electrode 1102 is the total surface area of the electrode per unit of mass (e.g., m²/kg), per unit of volume (e.g., m²/m³ or m$^{-1}$), or per unit of base area (e.g., m²/m²) As the specific surface area increases, the electrochemical capacitance ($C_{electrochemical}$) increases, and a greater amount of ions can be displaced with the same applied potential before the capacitor becomes charged. For example, the specific surface area of the working electrode may be increased by making the electrode "spongy."

Another way to increase $C_{electrochemical}$ is by increasing the base surface area of working electrode 1102. For example, if the working electrode has a cylindrical shape, then the base surface area of the cylinder may be increased. In another example, if the working electrode has a rectangular prism shape, then the base surface area of the rectangular prism may be increased. However, cell 1100 has a drawback. Working electrode 1102 and lipid bilayer 1114 have the same (or similar) base surface area or cross sectional area. When the base surface area of working electrode 1102 is increased, the base surface areas of the opening of well 1105 and lipid bilayer 1114 are both increased as well. As a result, both $C_{membrane}$ and $C_{electrochemical}$ are increased simultaneously. In other words, to optimize the overall system performance, $C_{membrane}$ cannot be reduced while maximizing $C_{electrochemical}$ by adjusting the base area of well 1105 alone.

In the present application, a non-faradaic electrochemical cell for nucleic acid sequencing that has a smaller aperture opening to a well for the formation of a lipid bilayer with a smaller base surface area and a working electrode with a larger base surface area is disclosed. The base surface area of the opening to the well (which is the same as the base surface area of the lipid bilayer) and the top base surface area of the working electrode that is exposed to the electrolyte can be adjusted independently of each other. Therefore, the two base surface areas may be adjusted independently to provide the desired ratio between $C_{membrane}$ and $C_{electrochemical}$ for optimized cell performance. A lipid bilayer is formed above the working electrode, and the lipid bilayer spans across a smaller aperture opening with a smaller base surface area than the top base surface area of the working electrode exposed to the electrolyte. With a smaller lipid bilayer base surface area and a larger working electrode top base surface area, $C_{membrane}$ can be reduced while maximizing $C_{electrochemical}$.

Figure 12:
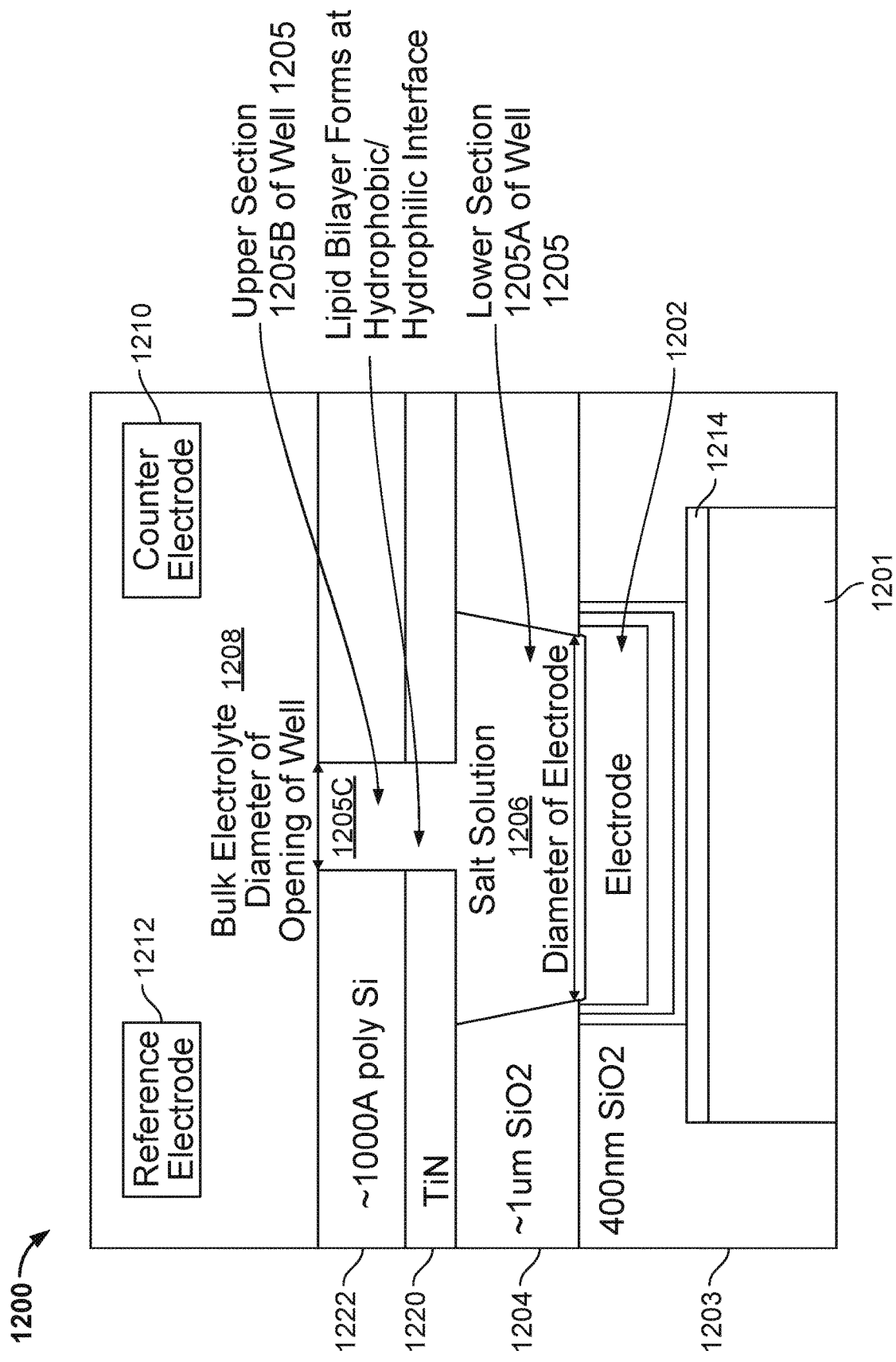
FIG. 12 illustrates a top view of a plurality of circular openings 1202 of a plurality of wells in a nanopore based sequencing chip.

FIG. 12 illustrates an embodiment of a non-faradaic electrochemical cell 1200 for nucleic acid sequencing that has a smaller aperture opening to a chalice well for the formation of a lipid bilayer with a smaller base surface area and a working electrode with a larger base surface area. Cell 1200 is one of the cells in a nanopore based sequencing chip. In contrast to cell 1100, $C_{membrane}$ and $C_{electrochemical}$ in cell 1200 may be adjusted independently by adjusting the base surface area of the membrane and the base surface area of the working electrode separately. Cell 1200 includes a conductive or metal layer 1201. Metal layer 1201 connects cell 1200 to the remaining portions of the nanopore based sequencing chip. In some embodiments, metal layer 1201 is the metal 6 layer (M6). Cell 1200 further includes a working electrode 1202 and a dielectric layer 1203 above metal layer 1201. In some embodiments, the base surface area of working electrode 1202 is circular or octagonal in shape and dielectric layer 1203 forms the walls surrounding working electrode 1202. Cell 1200 further includes a dielectric layer 1204 above working electrode 1202 and dielectric layer 1203. Dielectric layer 1204 forms the insulating wall surrounding a lower section (1205A) of a well 1205. In some embodiments, dielectric layer 1203 and dielectric layer 1204 together form a single piece of dielectric. Dielectric layer 1203 is the portion that is disposed horizontally adjacent to working electrode 1202, and dielectric layer 1204 is the portion that is disposed above the working electrode. In some embodiments, dielectric layer 1203 and dielectric layer 1204 are separate pieces of dielectric and they may be grown separately. Dielectric material used to form dielectric layers 1203 and 1204 includes glass, oxide, silicon mononitride (SiN), Silicon dioxide ($SiO_2$), and the like.

Cell 1200 further includes a hydrophilic layer 1220 (e.g., titanium nitrate, TiN) and a hydrophobic layer 1222 above dielectric layer 1204. Hydrophilic layer 1220 and hydrophobic layer 1222 together form the insulating wall surrounding an upper section (1205B) of well 1205. Hydrophilic layer 1220 and hydrophobic layer 1222 together form an overhang above the lower section (1205A) of well 1205. Alternatively, hydrophilic layer 1220 is optional. Hydrophobic layer 1222 forms the insulating wall surrounding upper section 1205B of well 1205. Hydrophobic layer 1222 forms an overhang above the lower section (1205A) of well 1205. In some embodiments, hydrophobic layer 1222 is formed by silanization. Alternatively, dielectric material that is hydrophobic such as hafnium oxide and polycrystalline silicon (poly-Si) may be used to form hydrophobic layer 1222. In some embodiments, hydrophobic layer 1222 has a thickness of about 1.5 nanometer (nm). Hydrophobic layer 1222 has a thickness between 100 angstroms to 2 microns. The interface between hydrophobic layer 1222 and hydrophilic layer 1220 facilitates the formation of a lipid bilayer. The lipid bilayer is formed at the interface between hydrophobic layer 1222 and hydrophilic layer 1220.

The upper section 1205B of well 1205 has an opening 1205C above the working electrode. In some embodiments, opening 1205C above the working electrode is circular and the base surface area of the opening is $\pi*(d/2)^2$, where d is the diameter of the opening. FIG. 13 illustrates a top view of a plurality of circular openings 1302 of a plurality of wells in a nanopore based sequencing chip. In some embodiments, opening 1205C above the working electrode is octagonal in shape. The base surface areas of opening 1205C and the upper section 1205B of well 1205, respectively, are smaller than the bottom base surface area of the lower section 1205A of well 1205. As the lipid bilayer spans across opening 1205C, a reduction in the base surface area of opening 1205C results in a reduction in the base surface area of the lipid bilayer and also the capacitance associated with the lipid bilayer. The lower section 1205A of well 1205 provides a large reservoir/chalice with a bottom base surface area larger than that in the upper section 1205B of well 1205. An increase in the bottom base surface area of the lower section 1205A of well 1205 increases the top base surface area of the electrode that has direct contact with the electrolye/salt solution 1206, thereby increasing the electrochemical capacitance associated with the working electrode.

Inside well 1205, salt solution/electrolyte 1206 is deposited above working electrode 1202. Salt solution 1206 may include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$). In some embodiments, salt solution 1206 has a thickness of about three microns (μm). The thickness of salt solution 1206 may range from 0-5 microns.

A bulk electrolyte 1208 containing protein nanopore transmembrane molecular complexes (PNTMC) and the analyte of interest is placed directly above the well. A single PNTMC/nanopore is inserted into the lipid bilayer by electroporation. The nanopore crosses the lipid bilayer and provides the only path for ionic flow from bulk electrolyte 1208 to working electrode 1202. Bulk electrolyte 1208 may further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Cell 1200 includes a counter electrode (CE) 1210. Cell 1200 also includes a reference electrode 1212, which acts as an electrochemical potential sensor. In some embodiments, counter electrode 1210 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

In some embodiments, working electrode 1202 is a titanium nitride (TiN) working electrode with increased electrochemical capacitance. The electrochemical capacitance associated with working electrode 1202 may be increased by maximizing the specific surface area of the electrode. The specific surface area of working electrode 1202 is the total surface area of the electrode per unit of mass (e.g., $m^2/kg$), per unit of volume (e.g., $m^2/m^3$ or $m^{-1}$), or per unit of base area (e.g., $m^2/m^2$). As the surface area increases, the electrochemical capacitance of the working electrode increases, and a greater amount of ions can be displaced with the same applied potential before the capacitor becomes charged. The surface area of working electrode 1202 may be increased by making the TiN electrode "spongy" or porous. The TiN sponge soaks up electrolyte and creates a large effective surface area in contact with the electrolyte.

FIGS. 14A-E illustrate an embodiment of a process 1400 for constructing a non-faradaic electrochemical cell (e.g., cell 1200) that has a smaller aperture opening to a well for the formation of a lipid bilayer with a smaller base surface area and a working electrode with a larger base surface area.

Figure 14A:
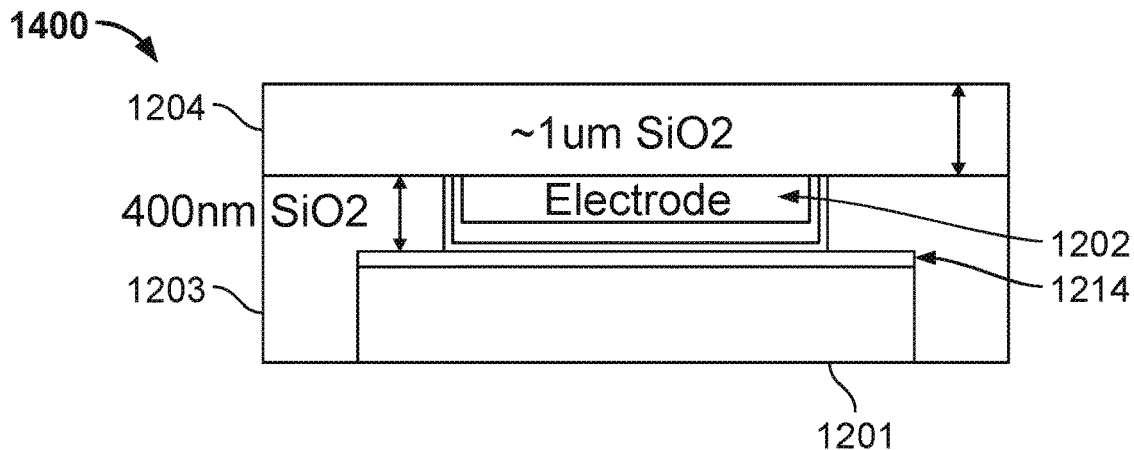
FIGS. 14A-E illustrate an embodiment of a process 1400 for constructing a non-faradaic electrochemical cell that has a smaller aperture opening to a well for the formation of a lipid bilayer with a smaller base surface area and a working electrode with a larger base surface area.

FIG. 14A illustrates step A of process 1400. In some embodiments, an optional anti-reflective layer (e.g., TiN) 1214 is disposed on top of a conductive layer 1201 (e.g., M6). A layer of dielectric 1203 (e.g., SiO$_2$) is disposed on top of conductive layer 1201 or the optional anti-reflective layer 1214. The conductive layer includes circuitries that deliver the signals from the cell to the rest of the chip. For example, the circuitries deliver signals from the cell to an integrating capacitor. In some embodiments, the layer of dielectric 1203 above conductive layer 1201 has a thickness of about 400 nm. The layer of dielectric 1203 is etched to create a hole. The hole provides a space for growing a spongy and porous electrode (e.g., a spongy TiN electrode). A spongy and porous TiN layer is deposited to fill the hole. The spongy and porous TiN layer is grown and deposited in a manner to create rough, sparsely-spaced TiN columnar structures or columns of TiN crystals that provide a high specific surface area that can come in contact with an electrolyte. The layer of spongy and porous TiN layer can be deposited using different deposition techniques, including atomic layer deposition, chemical vapor deposition, physical vapor deposition (PVD) sputtering deposition, and the like. The TiN layer may also be deposited by PVD sputtering deposition. For example, titanium can be reactively sputtered in an N$_2$ environment or directly sputtered from a TiN target. The conditions of each of the deposition methods may be tuned in such a way to deposit sparsely-spaced TiN columnar structures or columns of TiN crystals. For example, when the TiN layer is deposited by DC (direct current) reactive magnetron sputtering from a titanium (Ti) target, the deposition system can be tuned to use a low temperature, low substrate bias voltage (the DC voltage between the silicon substrate and the Ti target), and high pressure (e.g., 25 mT) such that the TiN can be deposited more slowly and more gently to form columns of TiN crystals. In some embodiments, the depth of the deposited TiN layer is about 1.5 times the depth of the hole. The depth of the deposited TiN layer is between 500 angstroms to 3 microns thick. The diameter or width of the deposited TiN layer is between 20 nm to 100 microns. The excess TiN layer is removed. For example, the excess TiN layer may be removed using chemical mechanical polishing (CMP) techniques. The remaining TiN deposited in the hole forms a spongy and porous TiN working electrode 1202. After working electrode 1202 is formed, a layer of dielectric 1204 (e.g, SiO$_2$) is deposited on top of the dielectric 1203 and working electrode 1202. In some embodiments, the depth of dielectric 1204 is between 100 nm to 2 microns.

Figure 14B:
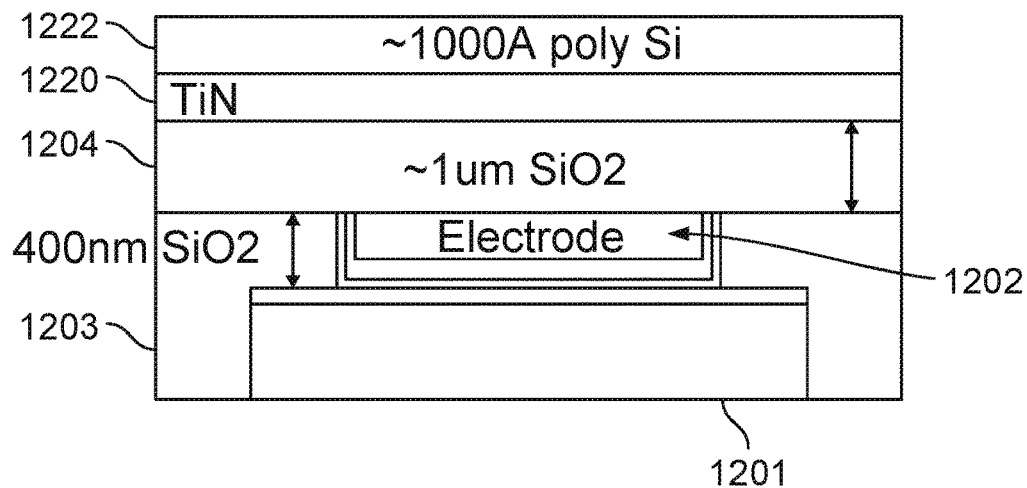

FIG. 14B illustrates step B of process 1400. A hydrophilic layer 1220 (e.g., titanium nitrate, TiN) is deposited above dielectric 1204. In some embodiments, hydrophilic layer 1220 has a thickness between 100 nm to 2 microns. A hydrophobic layer 1222 is deposited above hydrophilic layer 1220. In some embodiments, hydrophobic layer 1222 is formed by silanization. Alternatively, dielectric material that is hydrophobic such as hafnium oxide and polycrystalline silicon (poly-Si) may be used to form hydrophobic layer 1222. In some embodiments, hydrophobic layer 1222 has a thickness of about 1.5 nanometer (nm). Hydrophobic layer 1222 has a thickness between 100 angstroms to 2 microns. The hydrophobic layer and the hydrophilic layer provide two differentially functionalizable surfaces with different surface chemistry behaviors, thereby facilitating the formation of a lipid bilayer at the interface between the two layers.

Figure 14C:
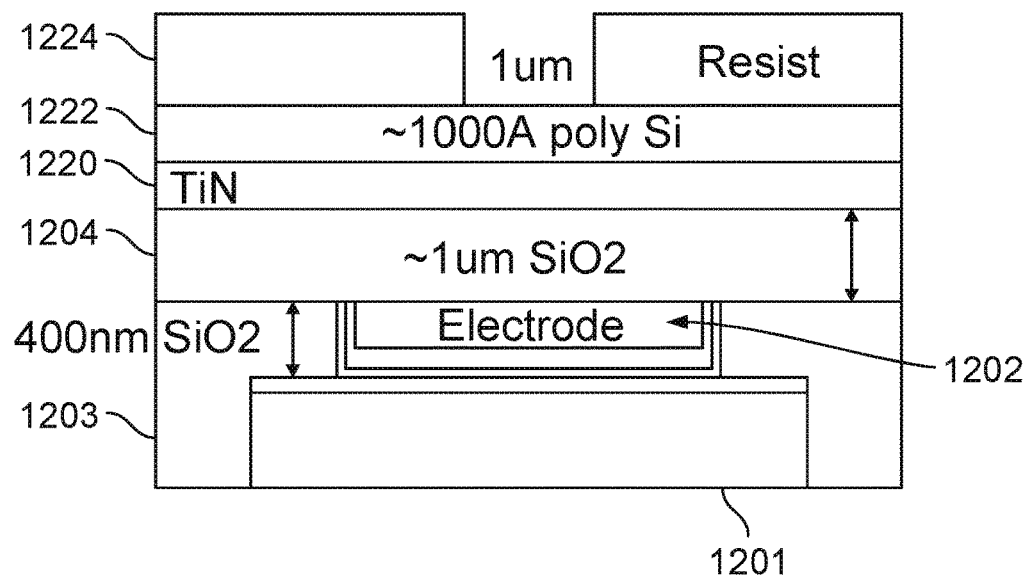

FIG. 14C illustrates step C of process 1400. A photoresist mask 1224 is deposited above hydrophobic layer 1222. The photoresist mask 1224 includes a pattern for etching the small aperture opening to a well. In some embodiments, the width of the pattern is selected to etch a small aperture opening with a width or diameter between 20 nm to 1 micron.

Figure 14D:
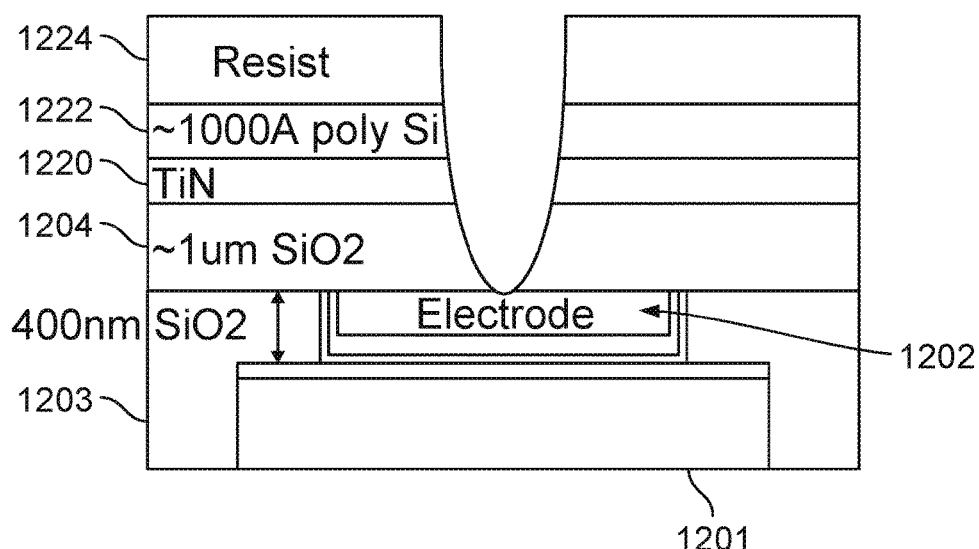

FIG. 14D illustrates step D of process 1400. Hydrophobic layer 1222, hydrophilic layer 1220, and dielectric 1204 are etched anisotropically using reactive ion etching (RIE). The etching is tuned (e.g., by tuning the etching time) to etch vertically close to but not reaching electrode 1202. The etching creates an initial well with a small aperture opening for the formation of the lipid bilayer.

Figure 14E:
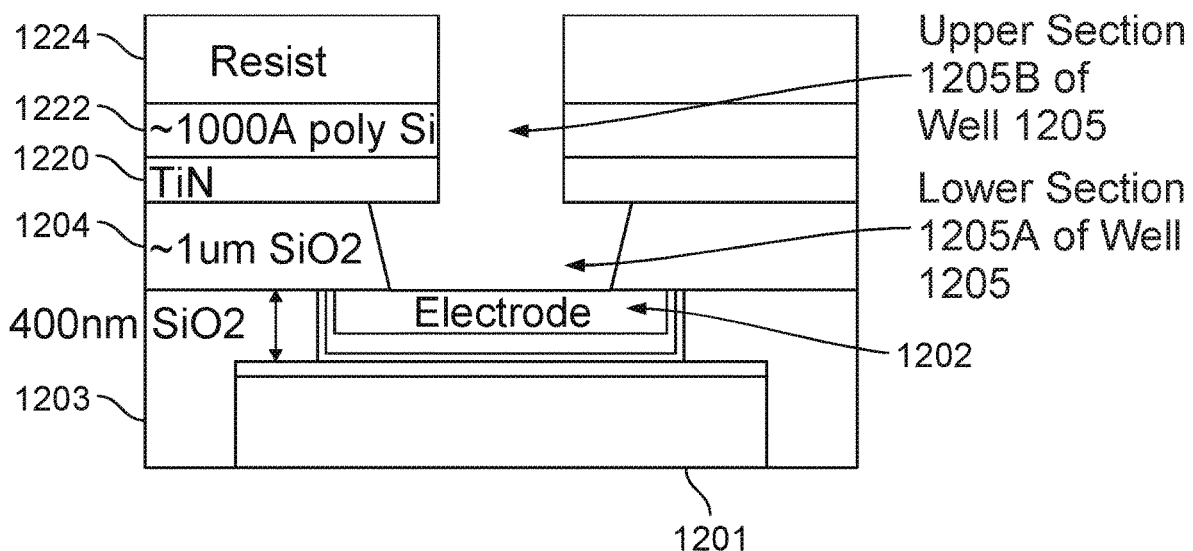

FIG. 14E illustrates step E of process 1400. Dielectric layer 1204 is isotropically etched to create a larger reservoir/chalice with a base surface area larger than that of the opening, enlarging the exposed electrode area while keeping the opening of the well small. In some embodiments, diluted hydrogen fluoride (dHF) or buffered oxide etch (BOE) is used as the wet etchant. The wet etchant selectively etches dielectric layer 1204 but not hydrophobic layer 1222 and hydrophilic layer 1220. Dielectric layer 1204 is made of a material that is differentially etchable from hydrophobic layer 1222 and hydrophilic layer 1220. The etching is tuned to etch horizontally about 200 nm from the edge of electrode 1202. The photoresist mask 1224 is then removed.

FIGS. 15A-E illustrate an embodiment of a process 1500 for constructing a non-faradaic electrochemical cell that has a smaller aperture opening to a well for the formation of a lipid bilayer with a smaller base surface area and a working electrode with a larger base surface area.

Figure 15A:
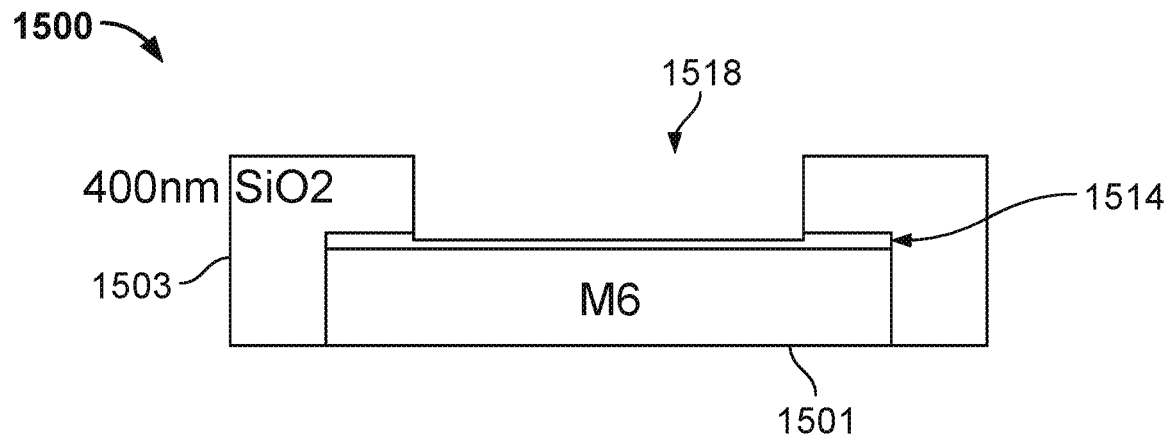
FIGS. 15A-F illustrate an embodiment of a process 1500 for constructing a non-faradaic electrochemical cell that has a smaller aperture opening to a well for the formation of a lipid bilayer with a smaller base surface area and a working electrode with a larger base surface area.

FIG. 15A illustrates step A of process 1500. In some embodiments, an optional anti-reflective layer (e.g., TiN) 1514 is disposed on top of a conductive layer 1501 (e.g., M6). A layer of dielectric 1503 (e.g., SiO$_2$) is disposed on top of conductive layer 1501 or the optional anti-reflective layer 1514. The conductive layer includes circuitries that deliver the signals from the cell to the rest of the chip. For example, the circuitries deliver signals from the cell to an integrating capacitor. In some embodiments, the layer of dielectric 1503 above conductive layer 1501 has a thickness of about 400 nm. The layer of dielectric 1503 is etched to create a hole 1518. The hole 1518 provides a space for growing an electrode, e.g., a spongy and porous electrode (e.g., a spongy TiN electrode) and a sacrifical layer.

Figure 15B:
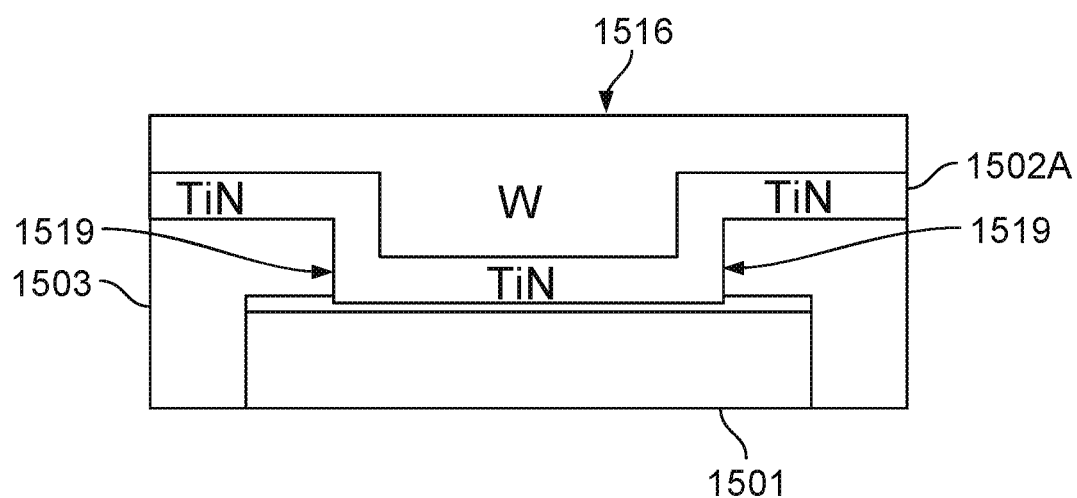

FIG. 15B illustrates step B of process 1500. A spongy and porous TiN layer 1502A is deposited to fill a portion of hole 1518. TiN layer 1502A further covers the vertical walls 1519 of hole 1518. TiN layer 1502A also covers the top surface of dielectric layer 1503. In some embodiments, the spongy and porous TiN layer is grown and deposited in a manner to create rough, sparsely-spaced TiN columnar structures or columns of TiN crystals that provide a high specific surface area that can come in contact with an electrolyte. The layer of spongy and porous TiN layer can be deposited using different deposition techniques, including atomic layer deposition, chemical vapor deposition, physical vapor deposition (PVD) sputtering deposition, and the like. The TiN layer may also be deposited by PVD sputtering deposition. For example, titanium can be reactively sputtered in an N$_2$ environment or directly sputtered from a TiN target. The conditions of each of the deposition methods may be tuned in such a way to deposit sparsely-spaced TiN columnar structures or columns of TiN crystals. For example, when the TiN layer is deposited by DC (direct current) reactive magnetron sputtering from a titanium (Ti) target, the deposition system can be tuned to use a low temperature, low substrate bias voltage (the DC voltage between the silicon substrate and the Ti target), and high pressure (e.g., 25 mT) such that the TiN can be deposited more slowly and more gently to form columns of TiN crystals. A layer of sacrifical layer 1516 is deposited. In some embodiments, sacrifical layer 1516 is a layer of tungsten or nickel. Sacrifical layer 1516 fills hole 1518 and covers the portion of TiN layer 1502A that covers the top surface of dielectric layer 1503.

Figure 15C:
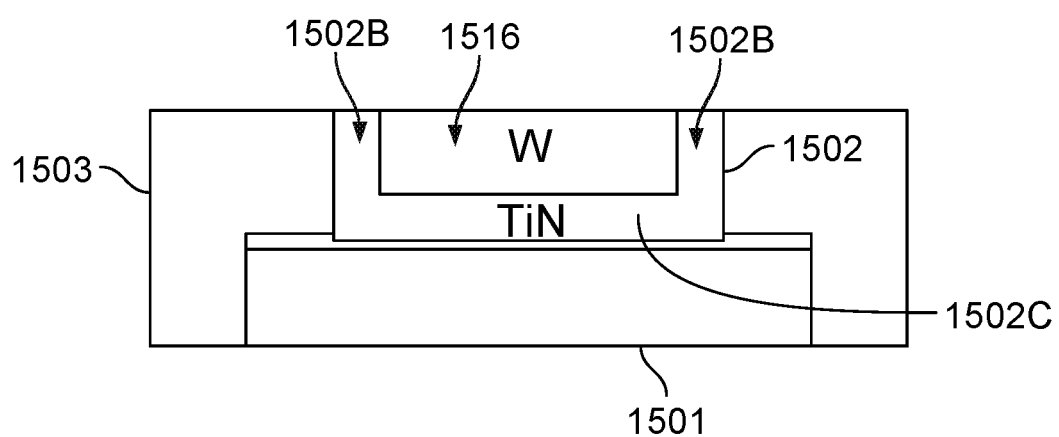

FIG. 15C illustrates step C of process 1500. The excess sacrifical layer 1516 and the excess TiN layer 1502A are removed, for example by chemical mechanical polishing (CMP) techniques, to create a coplanar surface. The remaining bottom TiN portion 1502C and the remaining vertical TiN portion 1502B form a spongy and porous TiN working electrode 1502. The diameter or width of working electrode 1502 is between 20 nm to 100 microns.

Figure 15D:
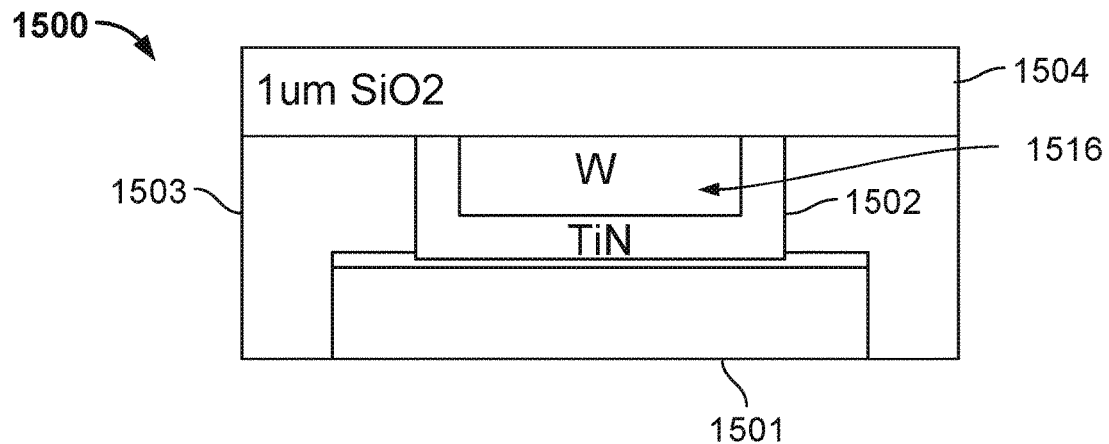

FIG. 15D illustrates step D of process 1500. A layer of dielectric 1504 (e.g, $SiO_2$) is deposited on top of the dielectric 1503, working electrode 1502, and sacrifical layer 1516. In some embodiments, the depth of dielectric 1504 is about 1 micron.

Figure 15E:
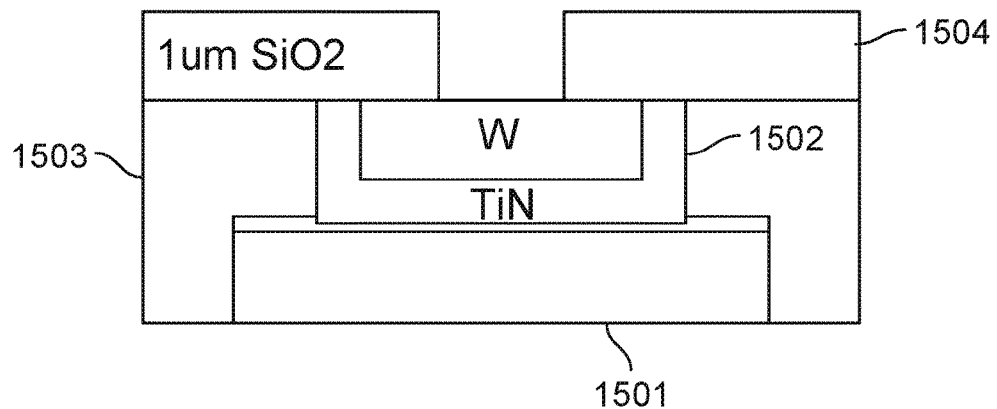

FIG. 15E illustrates step E of process 1500. A small aperture opening on dielectric layer 1504 is etched (e.g., using RIE) anisotropically to expose a portion of the sacrifical layer 1516. In some embodiments, the width of the small aperture opening is between 20 nm to 1 micron.

Figure 15F:
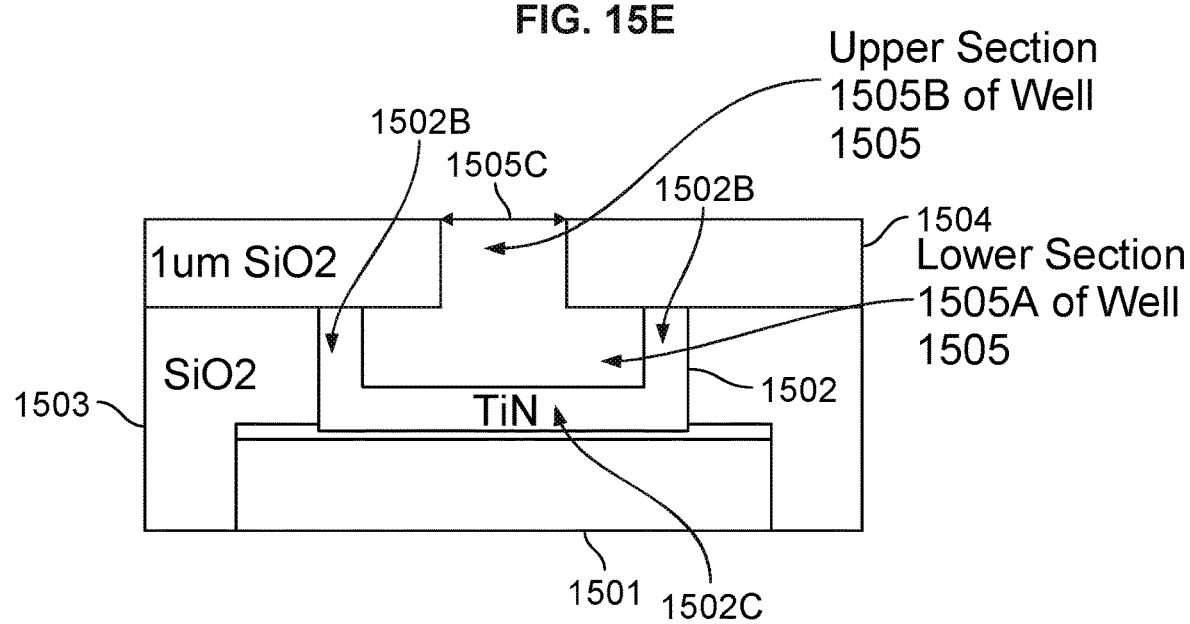

FIG. 15F illustrates step F of process 1500. Sacrificial layer 1516 is isotropically etched to create a larger reservoir/ chalice with a base surface area larger than that of the opening 1505C, enlarging the exposed electrode area while keeping the opening of the well small. Sacrificial layer 1516 is made of a material that is differentially etchable from dielectric layer 1504. In some embodiments, sacrificial layer 1516 is made of tungsten, and a selective etchant such as hot $H_2O_2$ is used as the wet etchant. The wet etchant selectively etches sacrificial layer 1516 without damaging dielectric layer 1504 and electrode 1502. The advantage of using a sacrificial layer 1516 is that the etching process is more robust and the process requires less tuning because over etching does not damage dielectric layer 1504 or working electrode 1502.

As shown in FIG. 15F, dielectric layer 1504 forms the insulating wall surrounding an upper section 1505B of a well 1505. Dielectric layer 1504 forms an overhang above a lower section (1505A) of well 1505. Dielectric layer 1503 forms the insulating wall surrounding a lower section (1505A) of a well 1505. Working electrode 1502 has a planar portion 1502C disposed at the bottom of the well. Planar portion 1502C has a top base surface area that is larger than the base surface area of opening 1505C. Working electrode 1502 has a vertical wall portion 1502B extending perpendicular from the planar portion 1502C at the peripheral of the planar portion 1502C. Vertical wall 1502B forms an electrode wall surrounding the lower section 1505A of well 1505. Vertical wall 1502B is adjacent to the insulating wall formed by dielectric layer 1503 and provides additional surface area that has contact with the electrolyte, thereby increasing the capacitance associated with the working electrode.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of constructing a nanopore cell, comprising:
   constructing a conductive layer;
   constructing a working electrode disposed above the conductive layer and at the bottom of a well configured to contain an electrolyte, such that at least a portion of a top base surface area of the working electrode is configured to be exposed to the electrolyte;
   constructing a first insulating wall disposed above the working electrode and surrounding a lower section of a well; and
   constructing a second insulating wall disposed above the first insulating wall and surrounding an upper section of the well, forming an overhang above the lower section of the well;
   wherein the working electrode comprises a planar portion disposed at the bottom of the well and further comprises a vertical wall portion extending perpendicular from the planar portion along the peripheral of the planar portion, and wherein the vertical wall portion forms an electrode wall surrounding the lower section the well, and wherein the vertical wall portion is adjacent to the first insulating wall; and
   wherein the first insulating wall is formed of a first material, and wherein the second insulating wall is formed of a second material, and wherein the working electrode is formed of a third material, and wherein a sacrificial layer is formed of a fourth material, and wherein constructing the first insulating wall and constructing the second insulating wall to form the lower section and the upper section of the well comprises:
   depositing a layer of first material above the conductive layer;
   etching a hole in the layer of first material above the conductive layer;
   depositing a layer of the third material to form the working electrode, wherein a portion of the layer of the third material covers a portion of the hole at its base, and wherein a portion of the layer of the third material covers a vertical wall of the hole;
   depositing a layer of the fourth material, filling the remaining portion of the hole;
   depositing a layer of the second material above the layer of first material, the working electrode, and the layer of the fourth material;
   etching the layer of the second material anisotropically to construct an initial well; and
   etching the layer of the fourth material isotropically, creating the lower section of the well.

2. The method of claim 1, wherein constructing the second insulating wall comprises:
   constructing an opening of the upper section of the well that is configured to support a membrane, and wherein a base surface area of the opening is smaller than the at least a portion of the top base surface area of the working electrode that is configured to be exposed to the electrolyte.

3. The method of claim 2, wherein a ratio of the base surface area of the opening and the at least a portion of the top base surface area of the working electrode is determined based on a predetermined ratio of a capacitance associated with the membrane and a capacitance associated with the working electrode.

4. The method of claim 1, wherein the first insulating wall is differentially etchable from the second insulating wall.

5. The method of claim 1, wherein constructing the second insulating wall comprises:

constructing a top layer and a bottom layer of the second insulating wall, and wherein the top layer comprises a hydrophobic layer, and wherein the bottom layer comprises a hydrophilic layer.

6. The method of claim 1, wherein constructing the second insulating wall comprises:

constructing a top layer and a bottom layer of the second insulating wall, and wherein the top layer and the bottom layer provide two differentially functionalizable surfaces with different surface chemistry behaviors that facilitate the formation of a membrane.

7. The method of claim 3, wherein the predetermined ratio of the capacitance associated with the membrane and the capacitance associated with the working electrode is adjusted by adjusting the capacitance associated with the working electrode.

8. The method of claim 7, wherein the capacitance associated with the working electrode is adjusted by adjusting a thickness and/or a surface area of the working electrode.

* * * * *